US012708289B2

(12) United States Patent
Wang et al.

(10) Patent No.: US 12,708,289 B2
(45) Date of Patent: Aug. 18, 2026

(54) WAIST SWINGING ESTIMATION DEVICE, ESTIMATION SYSTEM, WAIST SWINGING ESTIMATION METHOD, AND RECORDING MEDIUM

(71) Applicant: NEC Corporation, Tokyo (JP)

(72) Inventors: Zhenwei Wang, Tokyo (JP); Chenhui Huang, Tokyo (JP); Kazuki Ihara, Tokyo (JP); Kenichiro Fukushi, Tokyo (JP); Fumiyuki Nihey, Tokyo (JP); Hiroshi Kajitani, Tokyo (JP); Yoshitaka Nozaki, Tokyo (JP); Kentaro Nakahara, Tokyo (JP)

(73) Assignee: NEC CORPORATION, Tokyo (JP)

( * ) Notice: Subject to any disclaimer, the term of this patent is extended or adjusted under 35 U.S.C. 154(b) by 427 days.

(21) Appl. No.: 18/203,452

(22) Filed: May 30, 2023

(65) Prior Publication Data

US 2023/0397839 A1 Dec. 14, 2023

(30) Foreign Application Priority Data

Jun. 8, 2022 (JP) ................................ 2022-092755

(51) Int. Cl.
*A61B 5/11* (2006.01)
*A61B 5/00* (2006.01)

(52) U.S. Cl.
CPC ..... *A61B 5/1118* (2013.01); *A61B 2562/0219* (2013.01)

(58) Field of Classification Search
CPC .......... A61B 5/1118; A61B 2562/0219; A61B 5/6807; A61B 5/7267; A61B 5/112
See application file for complete search history.

(56) References Cited

U.S. PATENT DOCUMENTS

2011/0245633 A1 10/2011 Goldberg et al.
2015/0276793 A1* 10/2015 Takenaka ............ A61B 5/1121 73/504.03

(Continued)

FOREIGN PATENT DOCUMENTS

EP 4046570 A1 * 8/2022 .......... A61B 5/4082
JP 2012-024275 A 2/2012

(Continued)

OTHER PUBLICATIONS

Sun et al. "An Artificial Neural Network Framework for Lower Limb Motion Signal Estimation with Foot-Mounted Inertial Sensors", Mar. 2018 (Year: 2018).*

(Continued)

*Primary Examiner* — Eyob Hagos
(74) *Attorney, Agent, or Firm* — Sughrue Mion, PLLC

(57) ABSTRACT

Provided is a waist swinging estimation device including a communication unit that acquires feature amount data including a feature amount extracted from a gait waveform of a spatial acceleration and a spatial angular velocity included in sensor data regarding a movement of a foot of a subject and used for estimation of waist swinging that is an index regarding a movement of a waist, a storage unit that stores an estimation model that outputs an estimated value regarding the waist swinging according to an input of a feature amount included in the feature amount data, an estimation unit that inputs a feature amount included in the acquired feature amount data to the estimation model, and estimate waist swinging of the subject according to an estimated value regarding the waist swinging output from the estimation model, and an output unit that outputs information according to waist swinging of the subject.

20 Claims, 25 Drawing Sheets

(56) References Cited

U.S. PATENT DOCUMENTS

| | | | | |
|---|---|---|---|---|
| 2017/0188894 | A1 | 7/2017 | Chang et al. | |
| 2020/0222757 | A1* | 7/2020 | Yang | G06V 40/23 |
| 2021/0059569 | A1* | 3/2021 | Hiyama | A61B 5/7267 |
| 2022/0202369 | A1 | 6/2022 | Roche | |
| 2022/0330854 | A1* | 10/2022 | Jagannathan | G16H 50/20 |
| 2022/0379166 | A1* | 12/2022 | Lee | G06T 13/40 |
| 2024/0382806 | A1 | 11/2024 | Omid-Zohoor et al. | |

FOREIGN PATENT DOCUMENTS

| | | | |
|---|---|---|---|
| JP | 2017-006305 | A | 1/2017 |
| JP | 2018-121930 | A | 8/2018 |
| JP | 2020-151470 | A | 9/2020 |
| WO | 2020/240749 | A1 | 12/2020 |
| WO | 2021/225249 | A1 | 11/2021 |
| WO | 2022/038664 | A1 | 2/2022 |

OTHER PUBLICATIONS

JP Office Action for JP Application No. 2022-092755, mailed on Feb. 3, 2026 with English Translation.

JP Office Action for JP Application No. 2022-092755, mailed on Apr. 21, 2026 with English Translation.

US Office Action for U.S. Appl. No. 18/410,388, mailed on Apr. 15, 2026.

Office Action issued Apr. 24, 2026 in U.S. Appl. No. 18/411,116.

Japanese Official Communication for JP Application No. 2022-092755, issued on Jul. 7, 2026 with English Translation.

* cited by examiner

10
MEASUREMENT DEVICE
11
SENSOR
111
ACCELERATION SENSOR
112
ANGULAR VELOCITY SENSOR
12
FEATURE-AMOUNT-DATA GENERATION UNIT
121
ACQUISITION UNIT
122
NORMALIZATION UNIT
123
EXTRACTION UNIT
125
GENERATION UNIT
127
TRANSMISSION UNIT

Figure 10:
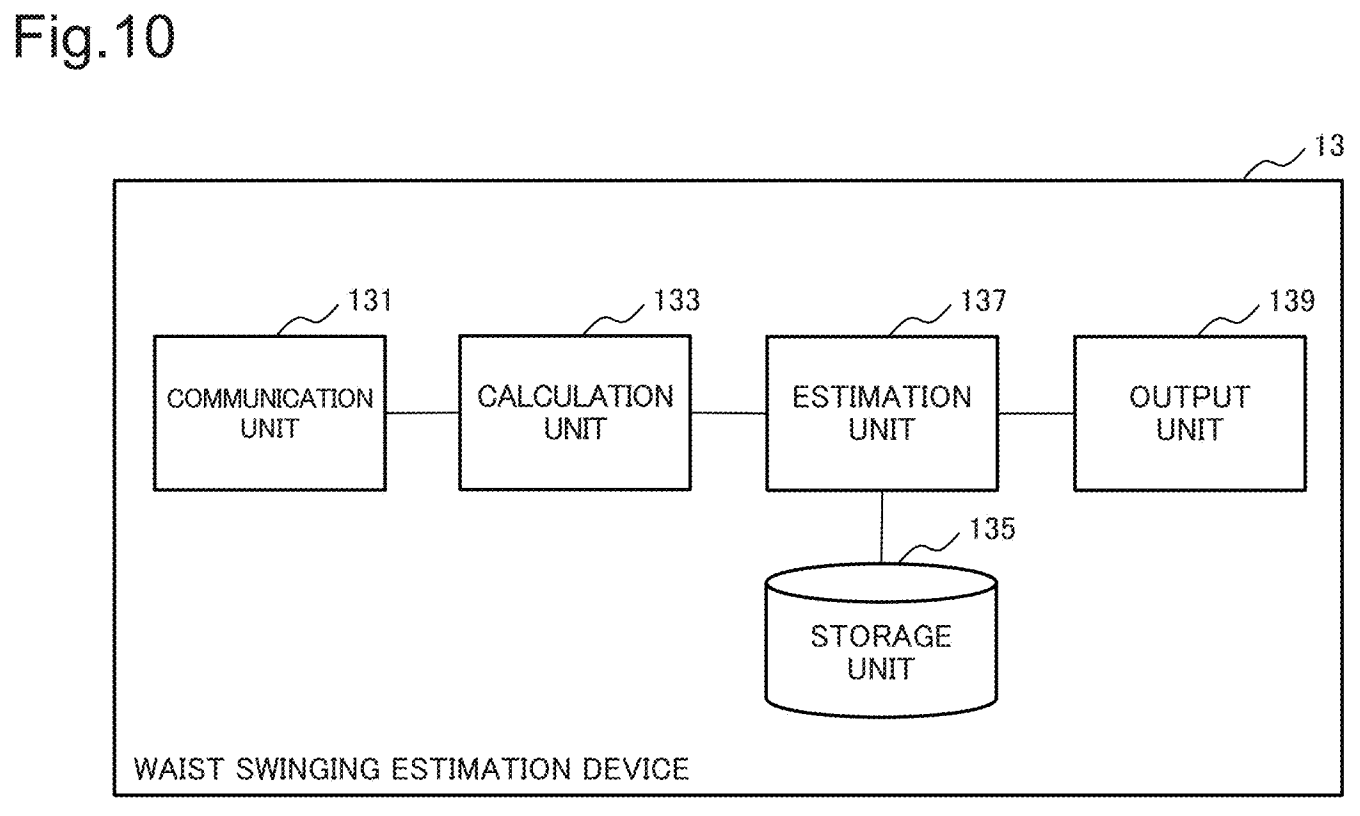

WAIST SWINGING ESTIMATION DEVICE

131 COMMUNICATION UNIT

133 CALCULATION UNIT

137 ESTIMATION UNIT

135 STORAGE UNIT

139 OUTPUT UNIT

Fig. 13

WAIST SWINGING (TRAVELING DIRECTION)

0

$dy_w$

0

50

100

GAIT CYCLE (%)

$dz_w$

100

50

0

GAIT CYCLE (%)

0

WAIST SWINGING (VERTICAL DIRECTION)

WAIST SWINGING (VERTICAL DIRECTION)

0

$dz_{w1}$ $dz_{w2}$

0

50

100

GAIT CYCLE (%)

Fig.18

| NUMBER | DATA | GAIT PHASE (%) |
|---|---|---|
| $F_{y1}$ | AVERAGE VALUE OF $A_y$ | 92–94 |
| $F_{y2}$ | AVERAGE VALUE OF $G_y$ | 76–81 |
| $F_{y3}$ | AVERAGE VALUE OF $G_z$ | 92 |
| $F_{y4}$ | DIFFERENCE OF $G_y$ | 91–92 |
| $F_{y5}$ | DIFFERENCE OF $G_z$ | 3 |

Fig.19

| NUMBER | DATA | GAIT PHASE (%) |
|---|---|---|
| $F_{x1}$ | AVERAGE VALUE OF $A_y$ | 62 |
| $F_{x2}$ | DIFFERENCE OF $E_y$ | 79-81 |

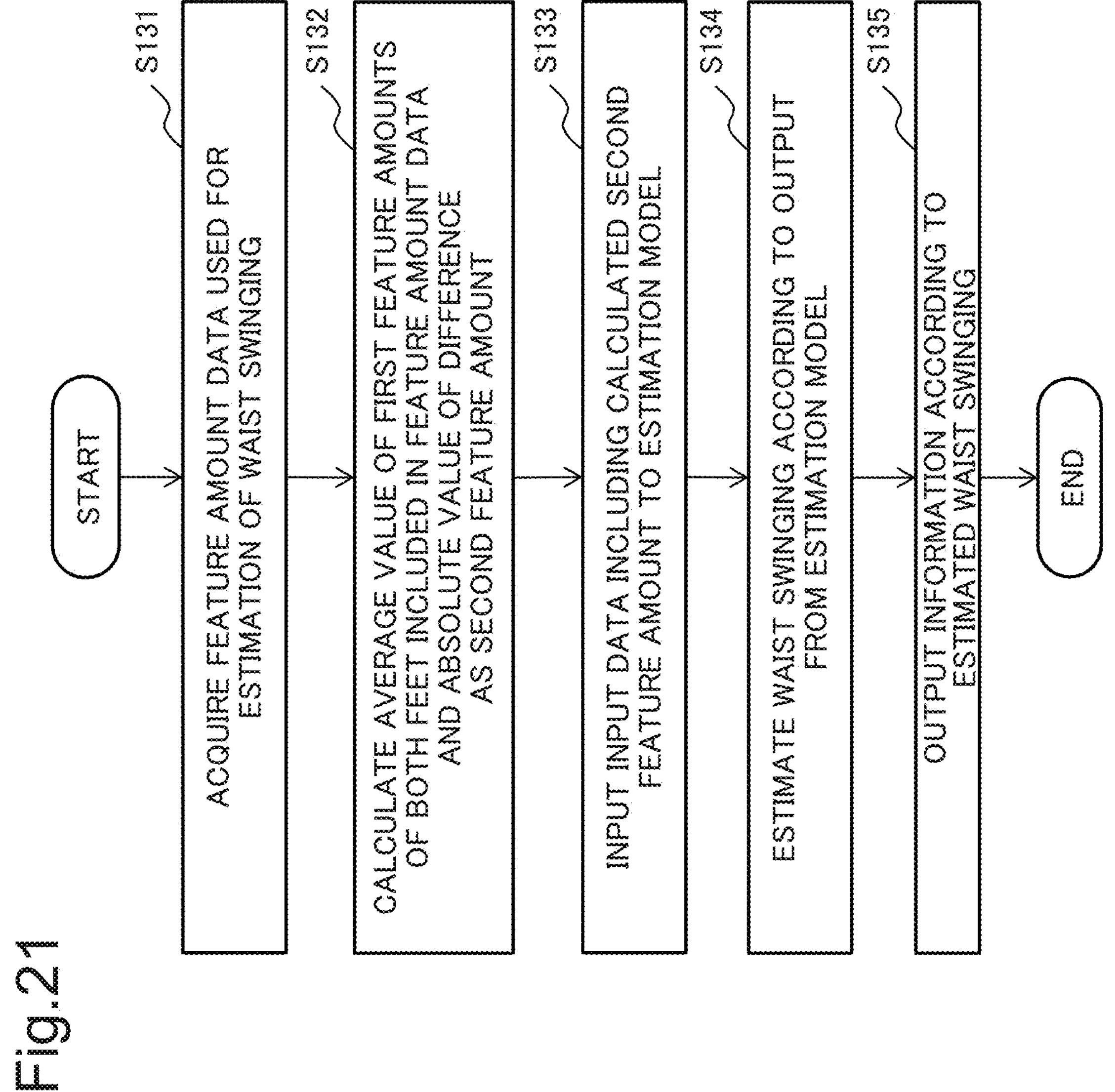
Fig.21
START
S131
ACQUIRE FEATURE AMOUNT DATA USED FOR ESTIMATION OF WAIST SWINGING
S132
CALCULATE AVERAGE VALUE OF FIRST FEATURE AMOUNTS OF BOTH FEET INCLUDED IN FEATURE AMOUNT DATA AND ABSOLUTE VALUE OF DIFFERENCE AS SECOND FEATURE AMOUNT
S133
INPUT INPUT DATA INCLUDING CALCULATED SECOND FEATURE AMOUNT TO ESTIMATION MODEL
S134
ESTIMATE WAIST SWINGING ACCORDING TO OUTPUT FROM ESTIMATION MODEL
S135
OUTPUT INFORMATION ACCORDING TO ESTIMATED WAIST SWINGING
END

WAIST SWINGING ESTIMATION DEVICE, ESTIMATION SYSTEM, WAIST SWINGING ESTIMATION METHOD, AND RECORDING MEDIUM

This application is based upon and claims the benefit of priority from Japanese Patent Application No. 2022-092755, filed on Jun. 8, 2022, the disclosure of which is incorporated herein in its entirety by reference.

TECHNICAL FIELD

The present disclosure relates to a waist swinging estimation device and the like that estimate waist swinging that is an index regarding waist movement.

BACKGROUND ART

With growing interest in healthcare, services that provide information according to gait have attracted attention. For example, a technique for analyzing a gait using sensor data measured by a sensor mounted on footwear such as shoes has been developed. In the time-series data of the sensor data, a feature associated with a gait event related to a physical condition appears. The physical condition of the subject can be estimated by analyzing the gait data including the features associated with the gait event.

Swinging of the waist in the front-back direction, the left-right direction, and the up-down direction (also referred to as waist swinging) during walking is an index indicating swinging or movement of the waist. The waist swinging is used as an index for visualization of gait and evaluation of gait stability. If the waist swinging can be estimated with high accuracy by analyzing the gait data, it is possible to provide a service according to the need for healthcare.

Patent Literature 1 (JP 2020-151470 A) discloses a gait evaluation device that evaluates gait ability of a user. The device of Patent Literature 1 calculates a plurality of gait indices related to a gait state using a plurality of pieces of gait data acquired from a subject. In the method of Patent Literature 1, a gait score of a subject is calculated using gait data acquired by an acceleration sensor attached to the waist of the subject. In the method of Patent Literature 1 a Harmonic Ratio, which is one of gait indices, is calculated from acceleration waveforms in the vertical direction, the lateral direction, and the longitudinal direction measured by an acceleration sensor attached to the waist of the subject.

In the method of Patent Literature 1, one of indices regarding the movement of the waist is measured using acceleration measured by an acceleration sensor attached to the waist. In daily life, sensors worn on the waist can limit free actions. If the position of the attached sensor deviates, the measurement accuracy decreases. Therefore, in the method of Patent Literature 1, it is not possible to easily measure the index regarding the movement of the waist with high accuracy in daily life.

An object of the present disclosure is to provide a waist swinging estimation device and the like that can easily estimate waist swinging as an index regarding movement of a waist with high accuracy in daily life.

SUMMARY

A waist swinging estimation device according to an aspect of the present disclosure incudes a communication unit configured to acquire feature amount data including a feature amount extracted from a gait waveform of a spatial acceleration and a spatial angular velocity included in sensor data regarding a movement of a foot of a subject and used for estimation of waist swinging that is an index regarding a movement of a waist, a storage unit configured to store an estimation model that outputs an estimated value regarding the waist swinging according to an input of a feature amount included in the feature amount data, and an estimation unit configured to input a feature amount included in the acquired feature amount data to the estimation model, and estimate waist swinging of the subject according to an estimated value regarding the waist swinging output from the estimation model, and an output unit configured to output information according to waist swinging of the subject.

In a waist swinging estimation method according to an aspect of the present disclosure, feature amount data including a feature amount extracted from sensor data regarding a movement of a foot of a subject and used for estimation of waist swinging that is an index regarding a movement of a waist is extracted, and an estimation model that outputs an estimated value regarding the waist swinging is stored according to an input of the feature amount data, the acquired feature amount data is inputted to the estimation model to estimate waist swinging of the subject according to an estimated value regarding the waist swinging output from the estimation model, and information according to waist swinging of the subject is outputted.

A program according to one aspect of the present disclosure causes a computer to execute: acquiring feature amount data including a feature amount to be used for estimation of waist swinging which is an index regarding a movement of a waist, the feature amount data being extracted from sensor data regarding a movement of a foot of a subject, storing an estimation model that outputs an estimated value related to the waist swinging according to an input of the feature amount data, inputting the acquired feature amount data to the estimation model and estimating waist swinging of the subject according to an estimated value regarding the waist swinging output from the estimation model, and outputting information according to waist swinging of the subject.

BRIEF DESCRIPTION OF THE DRAWINGS

Exemplary features and advantages of the present invention will become apparent from the following detailed description when taken with the accompanying drawings in which:

FIG. 10 is a block diagram illustrating an example of a configuration of a waist swinging estimation device included in the estimation system according to the first example embodiment;

FIG. 13 is a graph for explaining an example of a difference in waist swinging in the traveling direction;

FIG. 15 is a graph for explaining an example of a difference in waist swinging in a vertical direction;

FIG. 16 is a graph for explaining another example of the difference in waist swinging in the vertical direction;

FIG. 18 is a table summarizing a part of input data used for estimation of waist swinging in the traveling direction by the waist swinging estimation device included in the estimation system according to the first example embodiment;

FIG. 19 is a table summarizing a part of input data used for estimation of waist swinging in the left-right direction by the waist swinging estimation device included in the estimation system according to the first example embodiment;

FIG. 21 is a flowchart for explaining an example of the operation of the waist swinging estimation device included in the estimation system according to the first example embodiment;

EXAMPLE EMBODIMENT

Figure 1:
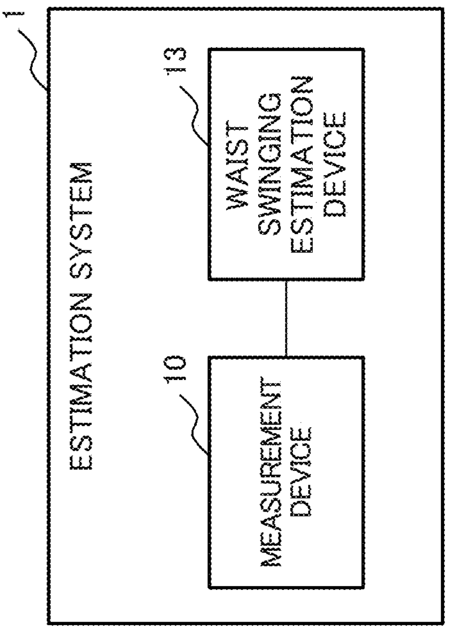
FIG. 1 is a block diagram illustrating an example of a configuration of an estimation system according to a first example embodiment.

Example embodiments of the present invention will be described below with reference to the drawings. In the following example embodiments, technically preferable limitations are imposed to carry out the present invention, but the scope of this invention is not limited to the following description. In all drawings used to describe the following example embodiments, the same reference numerals denote similar parts unless otherwise specified. In addition, in the following example embodiments, a repetitive description of similar configurations or arrangements and operations may be omitted.

First Example Embodiment

Next, an estimation system according to a first example embodiment will be described with reference to the drawings. The estimation system according to the present example embodiment measures sensor data regarding movement of a foot according to gait of a user by using a measurement device mounted on footwear. The estimation system of the present example embodiment estimates waist swinging that is an index regarding the movement of the waist using the measured sensor data. The waist swinging corresponds to a position difference (fluctuation width) of the waist based on an average position of the waist during walking.

The left and right feet are connected to the pelvis through the lower leg and the thigh. Hip and knee joints are located between the left and right feet and the pelvis, but the periodicity of the pelvis and the waist during walking is similar. Therefore, there is a phase in which the movement of the left and right feet and the movement of the waist interlock with each other. In the present example embodiment, waist swinging that is an index regarding the movement of the waist is estimated using sensor data regarding the movement of the foot. Details of the waist swinging will be described later.

(Configuration)

FIG. 1 is a block diagram illustrating an example of a configuration of an estimation system 1 according to the present example embodiment. The estimation system 1 includes a measurement device 10 and a waist swinging estimation device 13. In the present example embodiment, an example in which the measurement device 10 and the waist swinging estimation device 13 are configured as separate hardware will be described. For example, the measurement device 10 is installed on footwear or the like of a subject (user) who is an estimation target of waist swinging. For example, the function of the waist swinging estimation device 13 is installed in a mobile terminal carried by a subject (user). Hereinafter, the configurations of the measurement device 10 and the waist swinging estimation device 13 will be individually described.

[Measurement Device]

Figure 2:
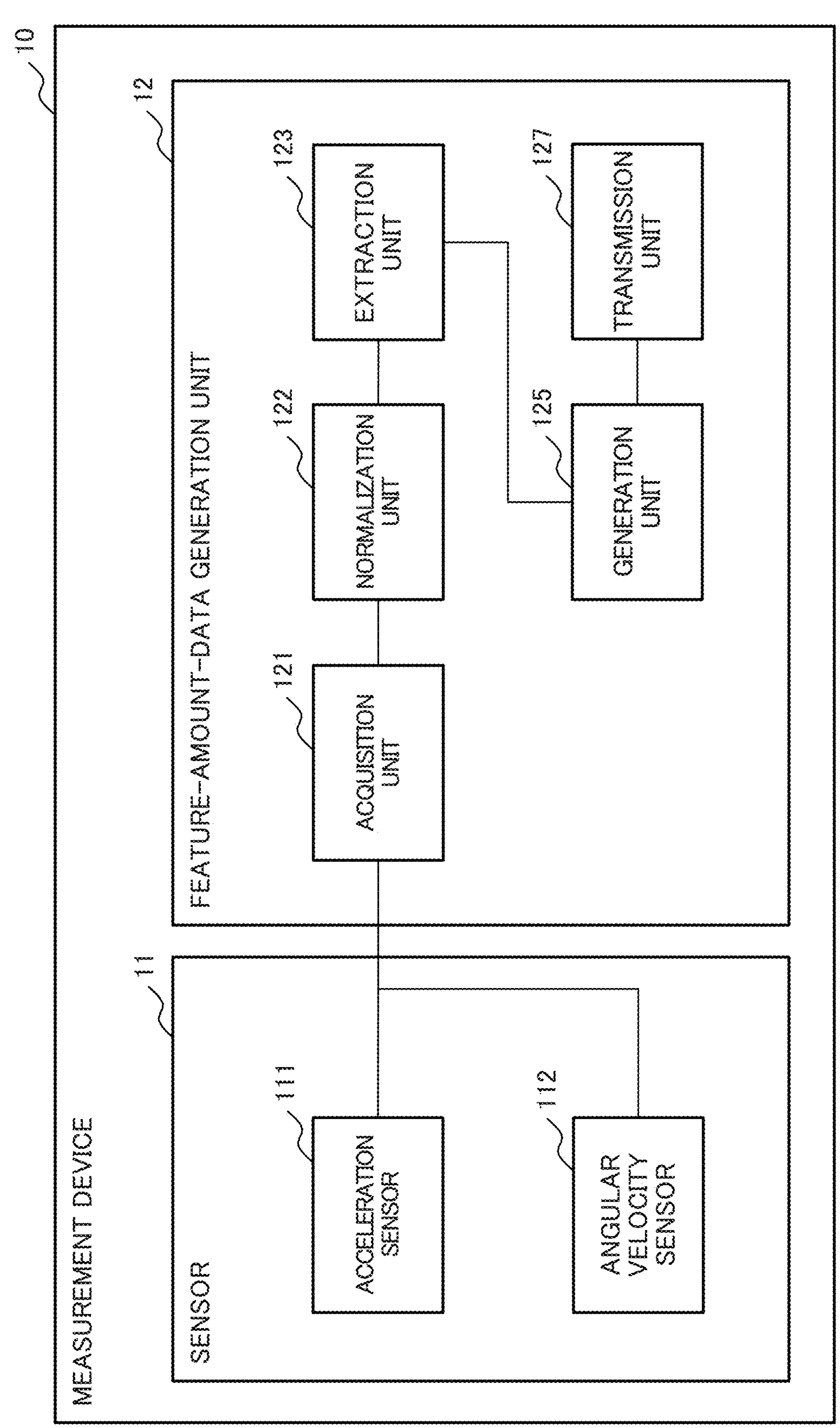
FIG. 2 is a block diagram illustrating an example of a configuration of a measurement device included in the estimation system according to the first example embodiment.

FIG. 2 is a block diagram illustrating an example of a configuration of the measurement device 10. The measurement device 10 includes a sensor 11 and a feature-amount-data generation unit 12. In the present example embodiment, an example in which the sensor 11 and the feature-amount-data generation unit 12 are integrated will be described. The sensor 11 and the feature-amount-data generation unit 12 may be provided as separate devices.

As illustrated in FIG. 2, the sensor 11 includes an acceleration sensor 111 and an angular velocity sensor 112. FIG. 2 illustrates an example in which the acceleration sensor 111 and the angular velocity sensor 112 are included in the sensor 11. The sensor 11 may include a sensor other than the acceleration sensor 111 and the angular velocity sensor 112. Sensors other than the acceleration sensor 111 and the angular velocity sensor 112 that can be included in the sensor 11 will not be described.

The acceleration sensor 111 is a sensor that measures accelerations (also referred to as spatial accelerations) in three axial directions. The acceleration sensor 111 measures an acceleration (also referred to as a spatial acceleration) as a physical quantity regarding the movement of the foot. The acceleration sensor 111 outputs the measured acceleration to the feature-amount-data generation unit 12. For example, a sensor of a piezoelectric type, a piezoresistive type, a capacitance type, or the like can be used as the acceleration sensor 111. The sensor used as the acceleration sensor 111 is not limited to the measurement method as long as the sensor can measure an acceleration.

The angular velocity sensor 112 is a sensor that measures an angular velocity (also referred to as a spatial angular velocity) around three axes. The angular velocity sensor 112 measures an angular velocity (also referred to as a spatial angular velocity) as a physical quantity regarding the movement of the foot. The angular velocity sensor 112 outputs the measured angular velocity to the feature-amount-data generation unit 12. For example, a sensor of a vibration type, a capacitance type, or the like can be used as the angular velocity sensor 112. The sensor used as the angular velocity sensor 112 is not limited to the measurement method as long as the sensor can measure the angular velocity.

The sensor 11 is achieved by, for example, an inertial measurement device that measures an acceleration and an angular velocity. An example of the inertial measurement device is an inertial measurement unit (IMU). The IMU includes the acceleration sensor 111 that measures an acceleration in three axial directions and the angular velocity sensor 112 that measures angular velocities around the three axes. The sensor 11 may be achieved by an inertial measurement device such as a vertical gyro (VG) or an attitude heading reference system (AHRS). The sensor 11 may be achieved by GPS/INS (Global Positioning System/Inertial Navigation System). The sensor 11 may be achieved by a device other than the inertial measurement device as long as it can measure a physical quantity regarding the movement of the foot.

Figure 3:
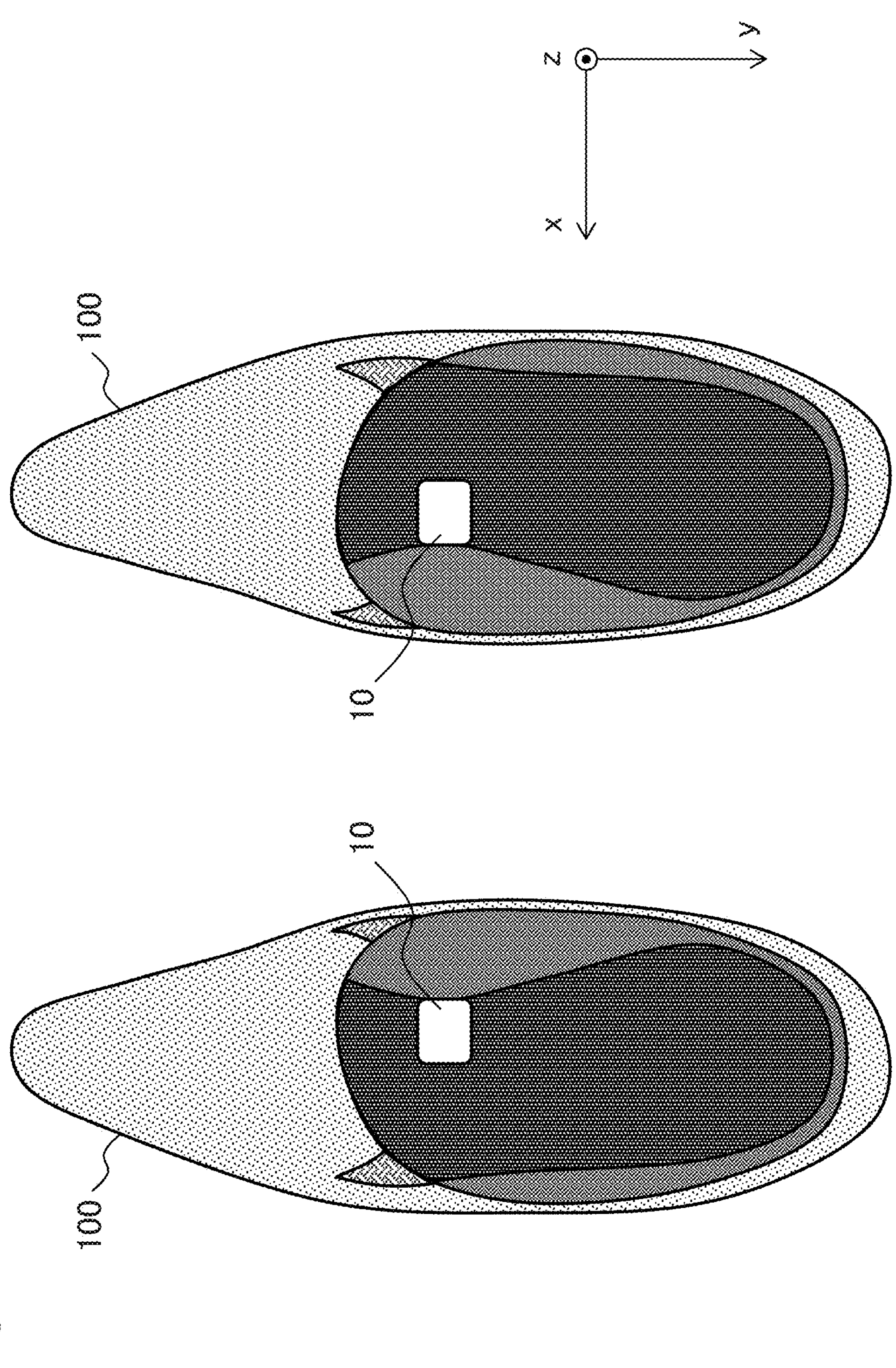
FIG. 3 is a conceptual diagram illustrating an arrangement example of the measurement device according to the first example embodiment.

FIG. 3 is a conceptual diagram illustrating an example in which the measurement device 10 is arranged in shoes 100 of both feet. In the example of FIG. 3, the measurement device 10 is installed at a position corresponding to the back side of the arch of foot. The measurement device 10 may be installed at a position other than the back side of the arch of the foot as long as the sensor data regarding the movement of the foot can be measured. For example, the measurement device 10 is disposed in an insole inserted into the shoe 100. The measurement device 10 may be disposed on the bottom surface of the shoe 100. The measurement device 10 may be embedded in the main body of the shoe 100. The measurement device 10 may be detachable from the shoe 100 or may not be detachable from the shoe 100. The measurement device 10 may be installed on a sock worn by the user or a decorative article such as an anklet worn by the user. The measurement device 10 may be directly attached to the foot or may be embedded in the foot. FIG. 3 illustrates an example in which the measurement devices are installed on the shoes 100 of both feet. The measurement device 10 may be installed on the shoe 100 of one foot.

In the example of FIG. 3, a local coordinate system including the x-axis in the left-right direction, the y-axis in the traveling direction, and the z-axis in the vertical direction is set with reference to the measurement device 10 (sensor 11). In the x-axis, the left side is positive, in the y-axis, the rear side is positive, and in the z-axis, the upper side is positive. The direction of the axis set in the sensor 11 may be the same for the left and right feet, or may be different for the left and right feet. For example, in a case where the sensors 11 produced with the same specifications are arranged in the left and right shoes 100, the vertical directions (directions in the Z-axis direction) of the sensors 11 arranged in the left and right shoes 100 are the same. In this case, the three axes of the local coordinate system set in the sensor data derived from the left foot and the three axes of the local coordinate system set in the sensor data derived from the right foot are the same on the left and right. In a case where the sensors 11 produced with different specifications on the left and right are disposed in the shoe 100, the vertical direction (direction in the Z-axis direction) of the sensors 11 disposed on the left and right shoes 100 may be different.

Figure 4:
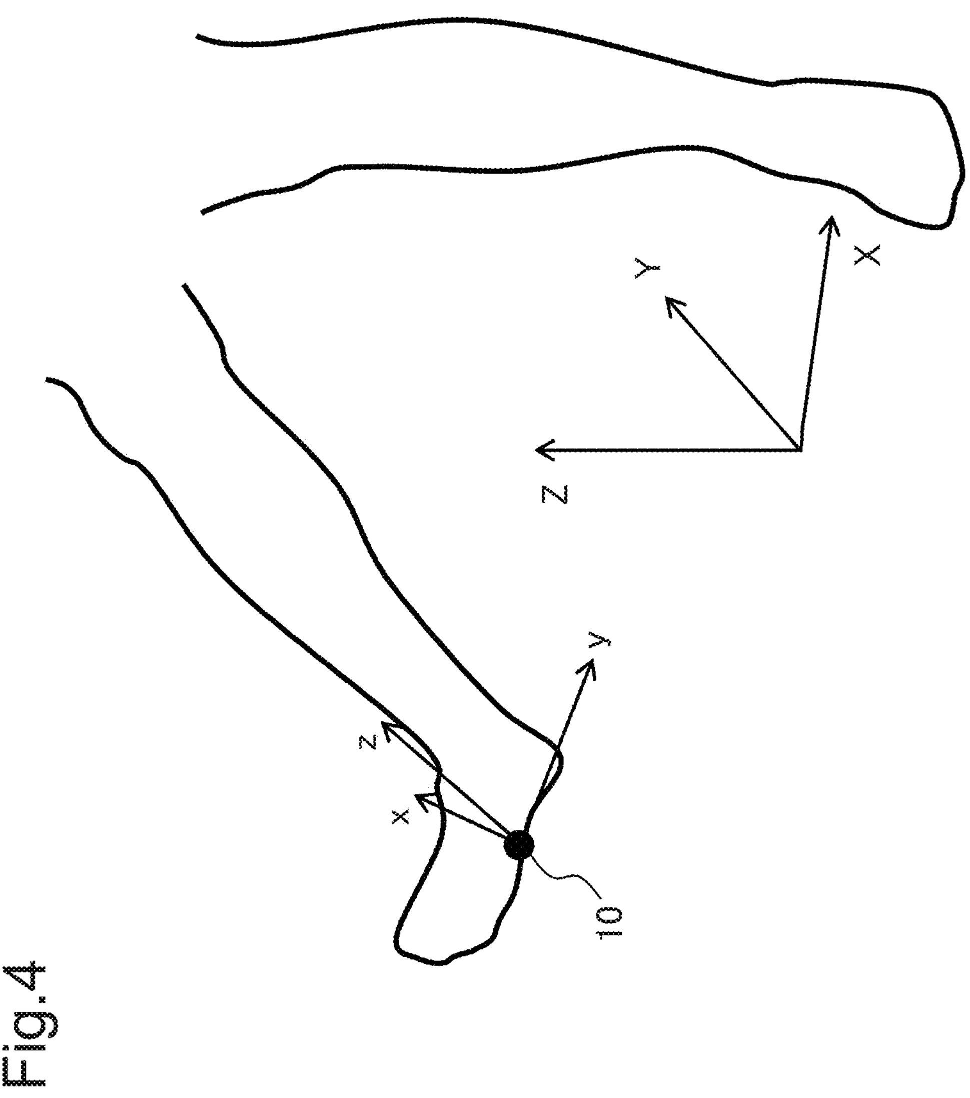
FIG. 4 is a conceptual diagram for explaining an example of a relationship between a local coordinate system and a world coordinate system set in the measurement device according to the first example embodiment.

FIG. 4 is a conceptual diagram for explaining a local coordinate system (x-axis, y-axis, z-axis) set in the measurement device 10 (sensor 11) installed on the back side of the arch of foot and a world coordinate system (X-axis, Y-axis, Z-axis) set with respect to the ground. In the world coordinate system (X-axis, Y-axis, Z-axis), in a state where the user facing the traveling direction is upright, the lateral direction of the user is set to the X-axis direction (the leftward direction is positive), the direction of the back surface of the user is set to the Y-axis direction (the backward direction is positive), and the gravity direction is set to the Z-axis direction (the vertically upward direction is positive). The example of FIG. 4 conceptually illustrates the relationship between the local coordinate system (x-axis, y-axis, z-axis) and the world coordinate system (X-axis, Y-axis, Z-axis), and does not accurately illustrate the relationship between the local coordinate system and the world coordinate system that varies depending on the gait of the user.

Figure 5:
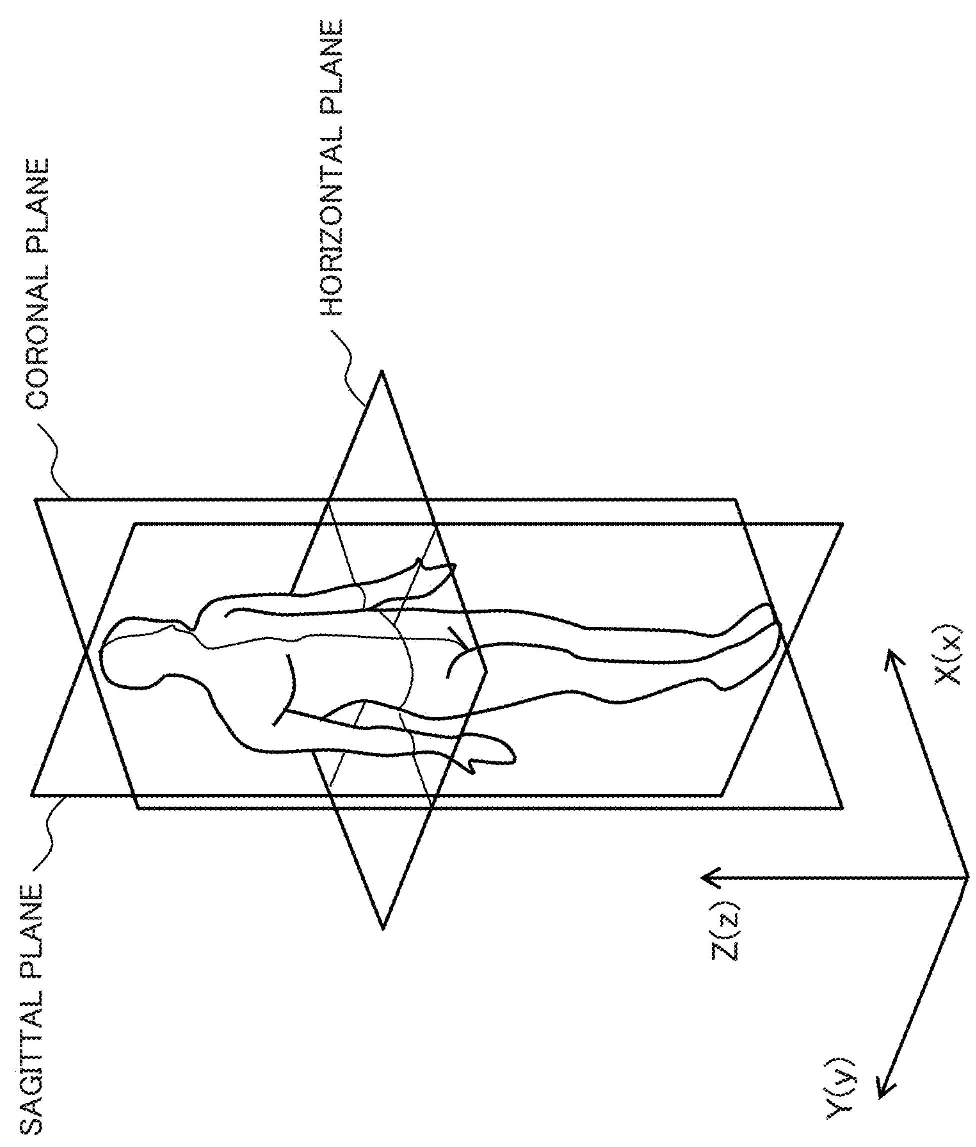
FIG. 5 is a conceptual diagram for explaining a human body surface.

FIG. 5 is a conceptual diagram for explaining a surface (also referred to as a human body surface) set for the human body. In the present example embodiment, a sagittal plane dividing the body into left and right, a coronal plane dividing the body into front and rear, and a horizontal plane dividing the body horizontally are defined. As illustrated in FIG. 5, the world coordinate system and the local coordinate system coincide with each other in a state in which the center line of the foot is oriented in the traveling direction. In the present example embodiment, rotation in the sagittal plane with the x-axis as the rotation axis is defined as roll, rotation in the coronal plane with the y-axis as the rotation axis is defined as pitch, and rotation in the horizontal plane with the z-axis as the rotation axis is defined as yaw. A rotation angle in the sagittal plane with the x-axis as a rotation axis is defined as a roll angle, a rotation angle in the coronal plane with the y-axis as a rotation axis is defined as a pitch angle, and a rotation angle in the horizontal plane with the z-axis as a rotation axis is defined as a yaw angle. In the following description, the x-axis, the y-axis, and the z-axis are expressed as three axes.

As illustrated in FIG. 2, the feature-amount-data generation unit 12 (also referred to as a feature-amount-data generation device) includes an acquisition unit 121, a normalization unit 122, an extraction unit 123, a generation unit 125, and a transmission unit 127. For example, the feature-amount-data generation unit 12 is achieved by a microcomputer or a microcontroller that performs overall control and data processing of the measurement device 10. For example, the feature-amount-data generation unit 12 includes a central processing unit (CPU), a random access memory (RAM), a read only memory (ROM), a flash memory, and the like. The feature-amount-data generation unit 12 controls the acceleration sensor 111 and the angular velocity sensor 112 to measure the angular velocity and the acceleration. For example, the feature-amount-data generation unit 12 may be implemented on a mobile terminal (not illustrated) carried by a subject (user). In this case, the sensor 11 may be provided with a communication function, and the sensor data transmitted from the sensor 11 may be received by the mobile terminal on which the feature-amount-data generation unit 12 is mounted.

The acquisition unit 121 acquires accelerations in three axial directions from the acceleration sensor 111. The acquisition unit 121 acquires angular velocities around three axes from the angular velocity sensor 112. For example, the acquisition unit 121 performs analog-to-digital conversion (AD conversion) on the acquired physical quantities (analog data) such as angular velocity and acceleration. The physical quantity (analog data) measured by the acceleration sensor 111 and the angular velocity sensor 112 may be converted into digital data in each of the acceleration sensor 111 and the angular velocity sensor 112. The acquisition unit 121 outputs the converted digital data (also referred to as sensor data) to the normalization unit 122. The acquisition unit 121 may be configured to store the sensor data in a storage unit (not illustrated). The sensor data includes at least acceleration data converted into digital data and angular velocity data converted into digital data. The acceleration data includes acceleration vectors in three axial directions. The angular velocity data includes angular velocity vectors around three axes. The acceleration data and the angular velocity data are associated with acquisition times of the data. The acquisition unit 121 may add correction such as a mounting error, temperature correction, and linearity correction to the acceleration data and the angular velocity data.

The normalization unit 122 acquires sensor data from the acquisition unit 121. The normalization unit 122 extracts time-series data (also referred to as gait waveform data) for one gait cycle from the time-series data of the acceleration in the three axial directions and the angular velocity around the three axes included in the sensor data. The normalization unit 122 normalizes (also referred to as first normalization) the time of the extracted gait waveform data for one gait cycle to a gait cycle of 0 to 100% (percent). The timing such as 1% or 10% included in the 0 to 100% gait cycle is also regarded as the gait phase. The normalization unit 122 normalizes (also referred to as second normalization) the first-normalized gait waveform data for one gait cycle so that the stance phase becomes 60% and the swing phase becomes 40%. The stance phase is a period in which at least a part of the back side of the foot is in contact with the ground. The swing phase is a period in which the back side of the foot is away from the ground. When the gait waveform data is subjected to the second normalization, it is possible to reduce the influence of the shift of the gait phase that may occur in each gait cycle.

Figure 6:
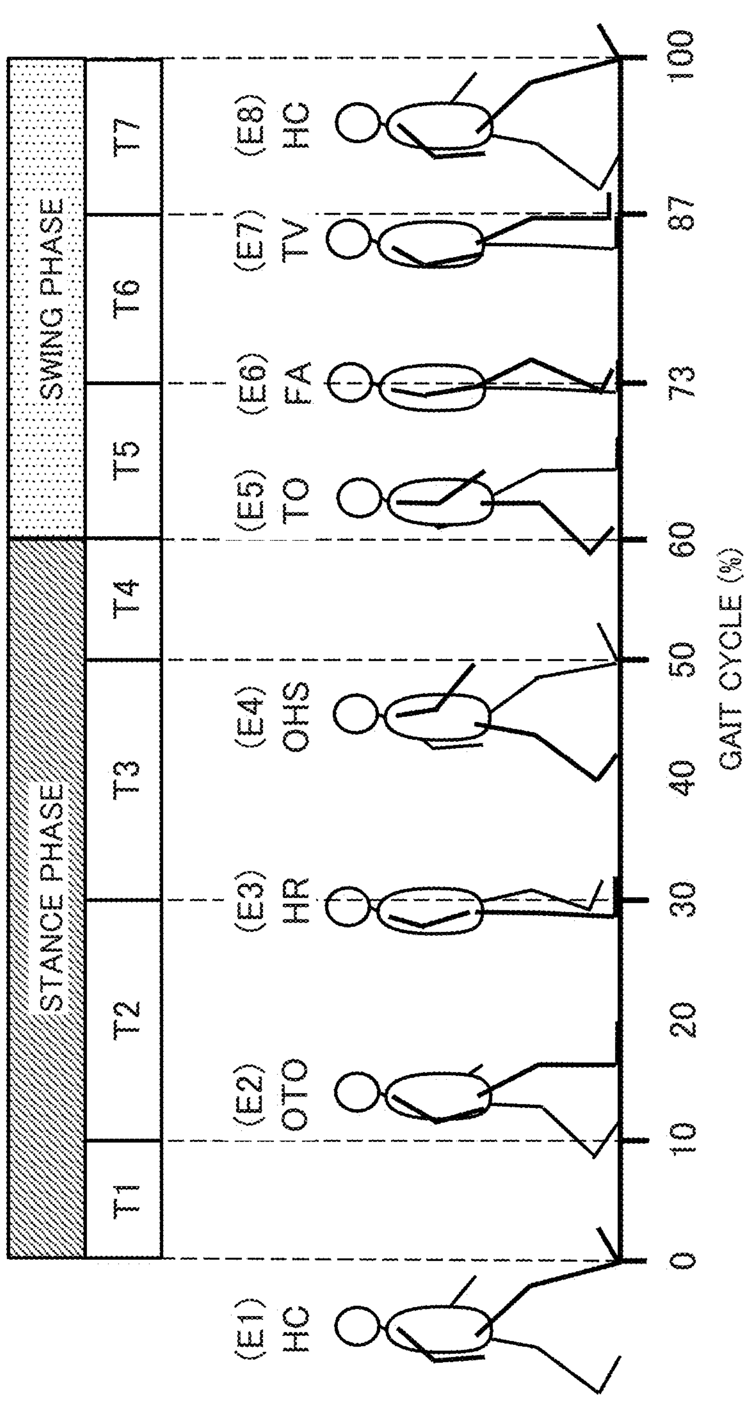
FIG. 6 is a conceptual diagram for explaining a gait cycle.

FIG. 6 is a conceptual diagram for explaining one gait cycle with the right foot as a reference. One gait cycle based on the left foot is also similar to that of the right foot. The horizontal axis of FIG. 6 is one gait cycle of the right foot with a time point at which the heel of the right foot lands on the ground as a starting point and a time point at which the heel of the right foot next lands on the ground as an ending point. The horizontal axis in FIG. 6 is first-normalized with one gait cycle as 100%. In the horizontal axis of FIG. 6, the second normalization is performed such that the stance phase is 60% and the swing phase is 40%. The one gait cycle of one foot is roughly divided into a stance phase in which at least a part of the back side of the foot is in contact with the ground and a swing phase in which the back side of the foot is separated from the ground. The stance phase is further subdivided into an initial stance period T1, a mid-stance period T2, a terminal stance period T3, and a pre-swing period T4. The swing phase is further subdivided into an initial swing period T5, amid-swing period T6, and a terminal swing period T7. FIG. 6 is an example, and does not limit the periods constituting one gait cycle, the names of these periods, and the like.

As illustrated in FIG. 6, in walking, a plurality of events (also referred to as gait events) occur. E1 represents an event in which the heel of the right foot touches the ground (HC: Heel Contact). E2 represents an event in which the toe of the left foot is separated from the ground with the sole of the right foot in contact with the ground (OTO: Opposite Toe Off). E3 represents an event in which the heel of the right foot lifts with the sole of the right foot in contact with the ground (HR: Heel Rise). E4 is an event in which the heel of the left foot is grounded (OHS: opposite heel strike). E5 represents an event in which the toe of the right foot is separated from the ground in a state where the sole of the left foot is grounded (TO: Toe Off). E6 represents an event in which the left foot and the right foot cross with the sole of the left foot in contact with the ground (FA: Foot Adjacent). E7 represents an event in which the tibia of the right foot is approximately perpendicular to the ground with the sole of the left foot in contact (TV: Tibia Vertical). E8 represents an event in which the heel of the right foot is grounded (HC: Heel Contact). E8 corresponds to the ending point of the gait cycle starting from E1 and corresponds to the starting point of the next gait cycle. FIG. 6 is an example, and does not limit events that occur during walking or names of these events.

Figure 7:
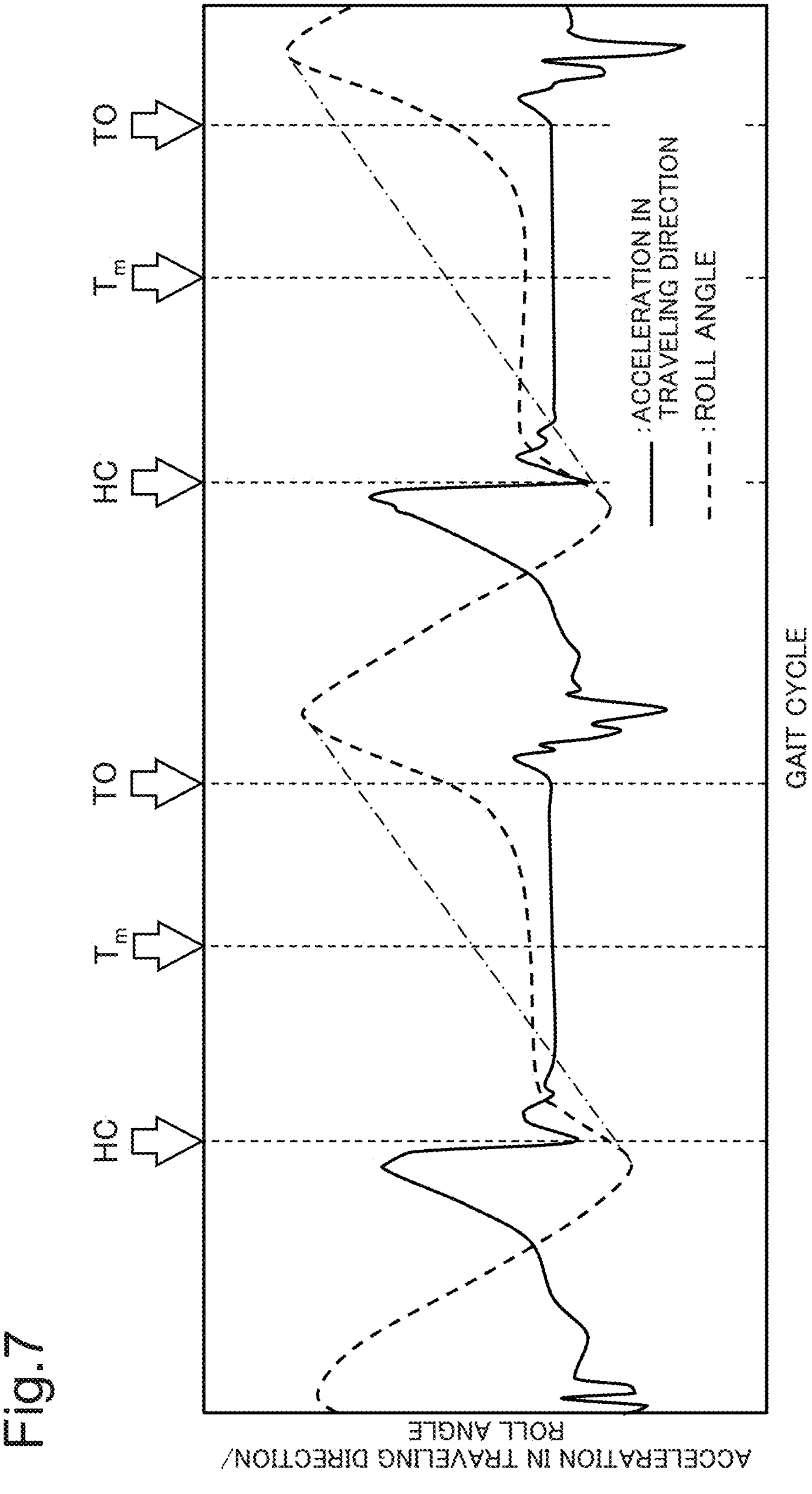
FIG. 7 is a graph for explaining an example of time-series data of sensor data measured by the measurement device according to the first example embodiment.
Figure 8:
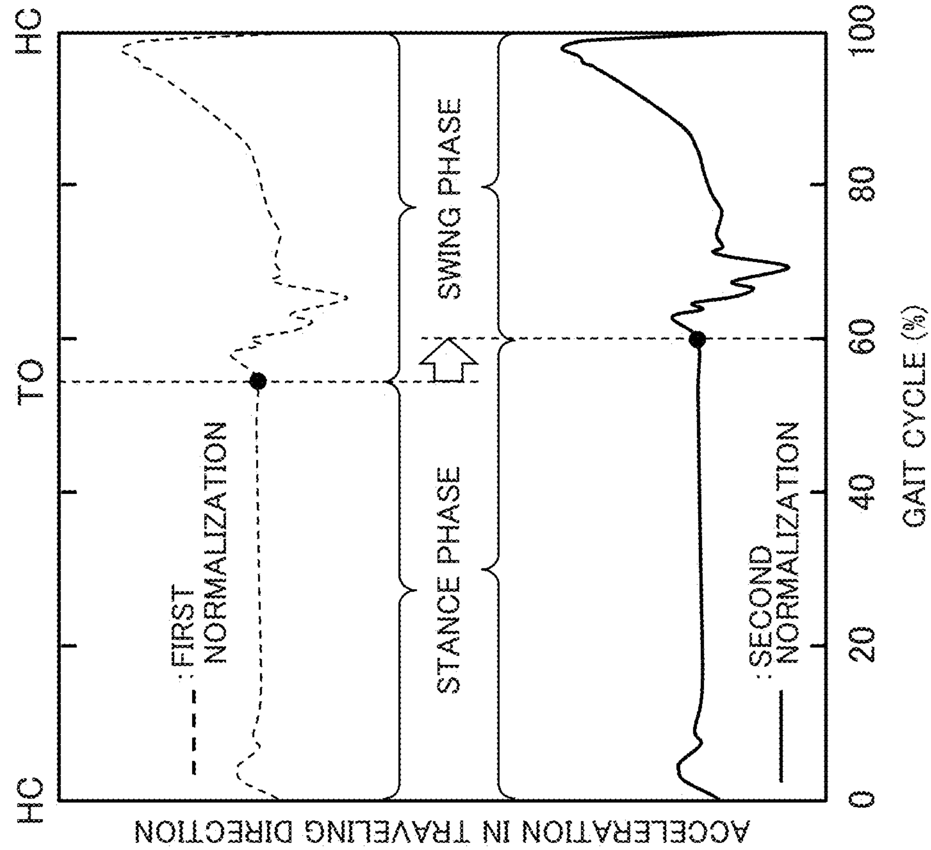
FIG. 8 is a diagram for explaining an example of normalization of gait waveform data by the measurement device according to the first example embodiment.

FIG. 7 is a diagram for explaining an example of detecting the heel contact HC and the toe off TO from the time-series data (solid line) of the acceleration in the traveling direction (acceleration in the Y direction). The timing of the heel contact HC is the timing of the local minimum peak immediately after the local maximum peak appearing in the time-series data of the acceleration in the traveling direction (acceleration in the Y direction). The local maximum peak serving as a mark of the timing of the heel contact HC corresponds to the local maximum peak of the gait waveform data for one gait cycle. A section between the consecutive heel contacts HC is one gait cycle. The timing of the toe off TO is the rising timing of the local maximum peak appearing after the period of the stance phase in which the fluctuation does not appear in the time-series data of the acceleration in the traveling direction (acceleration in the Y direction). FIG. 8 also illustrates time-series data (broken line) of the roll angle (angular velocity around the X-axis). The timing at the midpoint between the timing at which the roll angle is the minimum and the timing at which the roll angle is the maximum corresponds to a timing $T_m$ of the transition from the mid-stance period T2 to the terminal stance period T3. The timing $T_m$ of the transition from the mid-stance period T2 to the terminal stance period T3 substantially coincides with the timing of the heel rise HR. The parameter (also referred to as a gait parameter) used for the estimation of the physical condition can be obtained with reference to the timing $T_m$ of the transition from the mid-stance period T2 to the terminal stance period T3.

Figure 9:
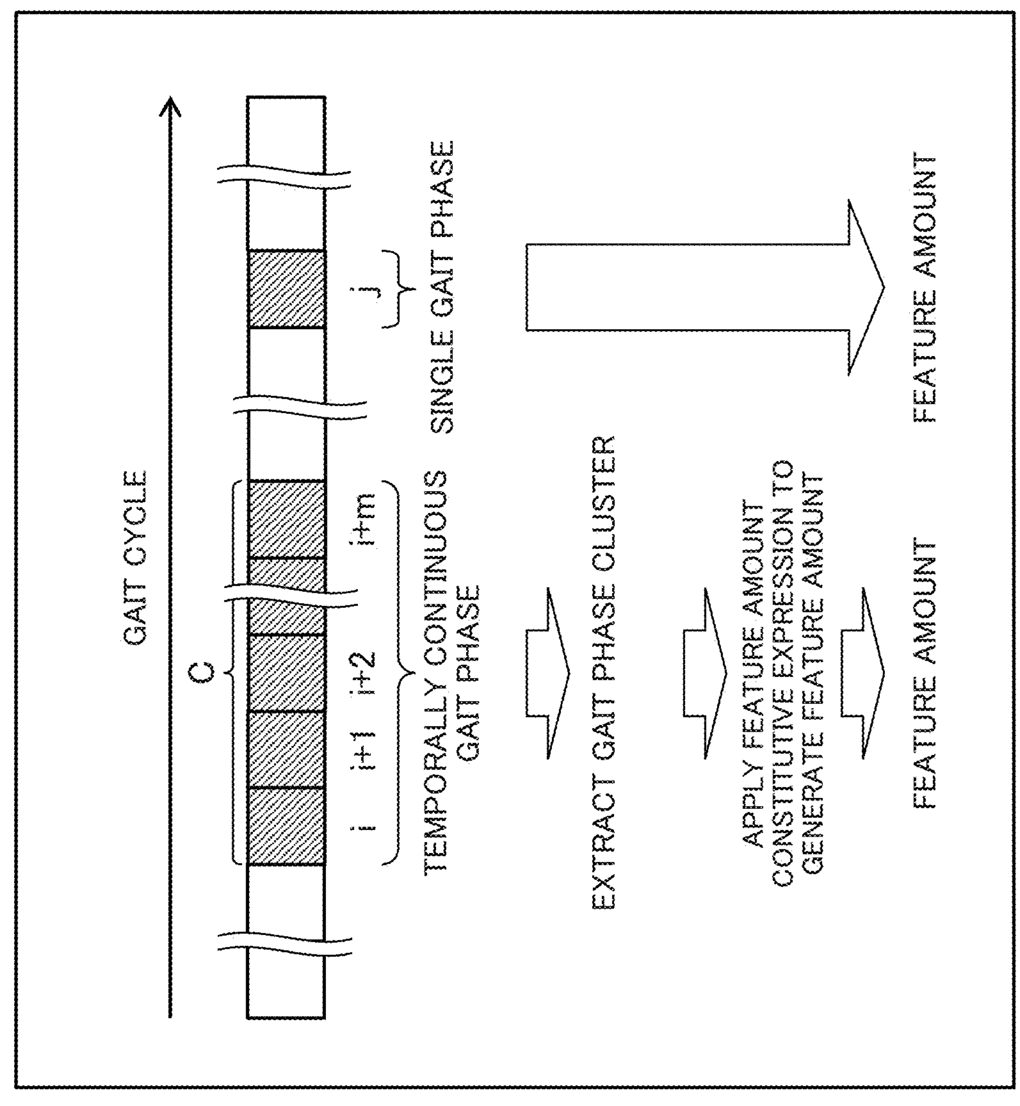
FIG. 9 is a conceptual diagram for explaining cluster feature amount extracted by a feature-amount-data generation unit of the measurement device according to the first example embodiment.

FIG. 8 is a diagram for explaining an example of normalization of gait waveform data. The normalization unit 122 detects the heel contact HC and the toe off TO from the time-series data of the acceleration in the traveling direction (acceleration in the Y direction). The normalization unit 122 extracts a section between consecutive heel contacts HC as gait waveform data for one gait cycle. The normalization unit 122 converts the horizontal axis (time axis) of the gait waveform data for one gait cycle into a gait cycle of 0 to 100% by the first normalization. In FIG. 9, the gait waveform data after the first normalization is indicated by a broken line. In the gait waveform data (broken line) after the first normalization, the timing of the toe off TO shifts from 60%.

In the example of FIG. 8, the normalization unit 122 normalizes a section from the heel contact HC in which the gait phase is 0% to the toe off TO subsequent to the heel contact HC to 0 to 60%. The normalization unit 122 normalizes a section from the toe off TO to the heel contact HC in which the gait phase subsequent to the toe off TO is 100% to 60 to 100%. As a result, the gait waveform data for one gait cycle is normalized to a section (stance phase) in which the gait cycle is 0 to 60% and a section (swing phase) in which the gait cycle is 60 to 100%. In FIG. 9, the gait waveform data after the second normalization is indicated by a solid line. In the gait waveform data (solid line) after the second normalization, the timing of the toe off TO coincides with 60%. For example, when the time of each of the stance phase and the swing phase and the ratio thereof are verified, the second normalization may be omitted.

FIGS. 7 and 8 illustrate examples in which the gait waveform data for one gait cycle is extracted/normalized based on the acceleration in the traveling direction (acceleration in the Y direction). Regarding acceleration/angular velocity other than the acceleration in the traveling direction (acceleration in the Y direction), the normalization unit 122 extracts/normalizes gait waveform data for one gait cycle in accordance with the gait cycle of the acceleration in the traveling direction (acceleration in the Y direction). The normalization unit 122 may generate time-series data of angles around three axes by integrating time-series data of angular velocities around the three axes. In this case, the normalization unit 122 also extracts/normalizes the gait waveform data for one gait cycle in accordance with the gait cycle of the acceleration in the traveling direction (acceleration in the Y direction) with respect to the angle around the three axes.

The normalization unit 122 may extract/normalize the gait waveform data for one gait cycle based on acceleration/angular velocity other than the acceleration in the traveling direction (acceleration in the Y direction) (not illustrated). For example, the normalization unit 122 may detect the heel contact HC and the toe off TO from the time-series data of the acceleration in the vertical direction (acceleration in the Z direction). The timing of the heel contact HC is a timing of a steep local minimum peak appearing in the time-series data of the acceleration in the vertical direction (acceleration in the Z direction). At the timing of the steep local minimum peak, the value of the acceleration in the vertical direction (acceleration in the Z direction) becomes substantially zero. The local minimum peak serving as a mark of the timing of the heel contact HC corresponds to the minimum peak of the gait waveform data for one gait cycle. A section between the consecutive heel contacts HC is one gait cycle. The timing of the toe off TO is a timing of an inflection point in the middle of gradually increasing after the time-series data of the acceleration in the vertical direction (acceleration in the Z direction) passes through a section with a small fluctuation after the local maximum peak immediately after the heel contact HC. The normalization unit 122 may extract/normalize the gait waveform data for one gait cycle based on both the acceleration in the traveling direction (acceleration in the Y direction) and the acceleration in the vertical direction (acceleration in the Z direction). The normalization unit 122 may extract/normalize the gait waveform data for one gait cycle based on acceleration, angular velocity, angle, and the like other than the acceleration in the traveling direction (acceleration in the Y direction) and the vertical direction acceleration (acceleration in the Z direction).

The extraction unit 123 acquires gait waveform data for one gait cycle normalized by the normalization unit 122. The extraction unit 123 extracts a feature amount used for estimation of waist swinging from the gait waveform data for one gait cycle. The extraction unit 123 extracts a feature amount (also referred to as a cluster feature amount) for each gait phase cluster from a gait phase cluster obtained by integrating temporally continuous gait phases based on a preset condition. The gait phase cluster includes at least one gait phase. The gait phase cluster also includes a single gait phase. The gait waveform data and the gait phase from which the feature amount used to estimate the waist swinging is extracted will be described later.

FIG. 9 is a conceptual diagram for explaining extraction of a feature amount for estimating waist swinging from gait waveform data for one gait cycle. For example, the extraction unit 123 extracts temporally continuous gait phases i to i+m as a gait phase cluster C (i and m are natural numbers). In the present example embodiment, an example will be described in which the gait phase cluster C used for estimation of the waist swinging is selected by correlation analysis using statistic parametric mapping. For example, the gait phase cluster C may be selected by Pearson's correlation analysis.

In the example of FIG. 9, the gait phase cluster C includes m gait phases (components). That is, the number of gait phases (components) (also referred to as the number of components) constituting the gait phase cluster C is m. FIG. 9 illustrates an example in which the gait phase has an integer value, but the gait phase may be subdivided into decimal places. When the gait phase is subdivided into decimal places, the number of components of the gait phase cluster C is a number corresponding to the number of data points in the section of the gait phase cluster. The extraction unit 123 extracts a feature amount from each of the gait phases i to i+m. In a case where the gait phase cluster C includes a single gait phase j, the extraction unit 123 extracts a feature amount from the single gait phase j (j is a natural number).

The generation unit 125 applies the feature amount constitutive expression to the feature amount extracted from each of the gait phases constituting the gait phase cluster to generate the feature amount (cluster feature amount) of the gait phase cluster. The cluster feature amount is also referred to as a first feature amount. The feature amount constitutive expression is a preset calculation expression for generating the feature amount of the gait phase cluster. For example, the feature amount constitutive expression is a calculation expression related to four arithmetic operations. For example, the cluster feature amount calculated using the feature amount constitutive expression is an integral average value, an arithmetic average value, a slope, a variation, or the like of the feature amount in each gait phase included in the gait phase cluster. For example, the generation unit 125 applies a calculation expression for calculating the slope or variation of the feature amount extracted from each of the gait phases constituting the gait phase cluster as the feature amount constitutive expression. For example, in a case where the gait phase cluster is configured by a single gait phase, it is not possible to calculate the slope or variation, and thus, it is sufficient to use a feature amount constitutive expression for calculating an integral average value, an arithmetic average value, or the like. For example, in a case where the gait phase cluster includes a single gait phase, the feature amount extracted from the gait phase may be set as the cluster feature amount.

The generation unit 125 calculates a parameter (also referred to as a gait parameter) regarding the gait. The generation unit 125 calculates the gait parameter using the feature amount derived from the gait waveform data. The gait parameter includes a feature used for estimation of a physical condition. The estimation system 1 may be configured to calculate the gait parameter on the side of the waist swinging estimation device 13. Hereinafter, examples of the gait parameters calculated by the generation unit 125 will be listed. The following gait parameters are merely examples, and do not cover all parameters including the features of the gait. In the present example embodiment, among the following gait parameters, those having a high correlation in the estimation of the waist swinging are selected. Details of the method for calculating the gait parameter will be omitted.

Examples of the gait parameter include a stride, a gait pitch, a gait speed, a grounding angle, a leaving angle, an outward turning distance (a dividing amount), and a toe direction (inward/outward turning). The stride is a distance between the toes of both feet in a state in which one of the left and right feet steps forward and the toe lands. The gait pitch is the number of steps within a predetermined time, and is used to calculate the gait speed. The gait speed is a moving speed in one gait cycle. The gait speed may be a value averaged in a plurality of gait cycles. The grounding angle is an angle (posture angle) of the sole with respect to the ground in a state where the heel is grounded. The grounding angle is an angle (posture angle) of the sole with respect to the ground in a state where the toe is grounded. The outward turning distance is a distance between a straight line indicating a moving route and a foot at a timing when the foot is farthest from the moving route of one foot in one gait cycle. The toe direction is an angle formed by a straight line indicating a moving route of one foot in one gait cycle and a center line of the foot in a landed state.

Examples of the gait parameter include a roll angle, a foot raising height, a maximum angular velocity in a plantarflexion direction, a maximum angular velocity in a dorsiflexion direction, a maximum speed, a leg information maximum acceleration during swinging, and cadence. For example, the heel contact or the roll angle at the toe off is used as the gait parameter. The foot raising height corresponds to the height of the foot in the vertical direction. For example, the maximum angular velocity in the plantarflexion direction and the maximum angular velocity in the dorsiflexion direction in the swing phase are used as the gait parameters. For example, the maximum speed in the swing phase is used as the gait parameter. The leg information maximum acceleration during swinging is the maximum value of the acceleration in the vertical direction of the leg during swinging, and relates to the rise of the waist according to the interlocking of the movement of the leg and the waist. The cadence corresponds to the number of steps in 60 seconds.

Examples of the gait parameter include a standing time, a swing time, a double support time (DST), a load time, a sole contact time, and a kicking time. The standing time is a time corresponding to the period of the stance phase. The swing time is a time corresponding to the period of the swing phase. The DST corresponds to a both-leg support period during walking. The DST includes a DST 1 corresponding to a both-leg support period after the heel contact and a DST 2 corresponding to a both-leg support period immediately before kicking. The load time is a time during which a load is applied to the sole of the foot. The load time corresponds to a time from the heel contact to the sole contact. The sole contact time is a time during which the main surface of the sole is in ground contact. The sole contact time corresponds to the time from the sole contact to the heel off. The kicking time is a time from application of a load to the main surface of the sole to kicking of the foot. The kicking time corresponds to the time from the sole contact to the toe off.

The transmission unit 127 outputs feature amount data including the cluster feature amount generated by the generation unit 125. In a case where the gait parameter is used to estimate the waist swinging, the transmission unit 127 outputs the feature amount data including the cluster feature amount and the gait parameter. The transmission unit 127 transmits the feature amount data to the waist swinging estimation device 13. For example, the transmission unit 127 transmits the feature amount data to the waist swinging estimation device 13 via wireless communication. For example, the transmission unit 127 is configured to transmit the feature amount data to the waist swinging estimation device 13 via a wireless communication function (not illustrated) conforming to a standard such as Bluetooth (registered trademark) or WiFi (registered trademark). The communication function of the transmission unit 127 may conform to a standard other than Bluetooth (registered trademark) or WiFi (registered trademark).

[Waist Swinging Estimation Device]

FIG. 10 is a block diagram illustrating an example of a configuration of the waist swinging estimation device 13. The waist swinging estimation device 13 includes a communication unit 131, a calculation unit 133, a storage unit 135, an estimation unit 137, and an output unit 139.

The communication unit 131 acquires the feature amount data from the measurement device 10. The communication unit 131 outputs the received feature amount data to the calculation unit 133. The communication unit 131 may receive the feature amount data from the measurement device 10 via a wire such as a cable, or may receive the feature amount data from the measurement device 10 via wireless communication. For example, the communication unit 131 is configured to receive the feature amount data from the measurement device 10 via a wireless communication function (not illustrated) conforming to a standard such as Bluetooth (registered trademark) or WiFi (registered trademark). The communication function of the communication unit 131 may conform to a standard other than Bluetooth (registered trademark) or WiFi (registered trademark).

The calculation unit 133 acquires the feature amount data. The calculation unit 133 calculates the input data used for estimation of the waist swinging using the cluster feature amount and the gait parameter included in the acquired feature amount data. The calculation unit 133 calculates an average value with respect to the first feature amounts for both feet used for estimation of waist swinging. The calculation unit 133 calculates the absolute value of the difference with respect to the first feature amount for both feet used for estimation of the waist swinging. The calculation unit 133 calculates an average value with respect to the gait parameter for both feet used for estimation of the waist swinging. The calculation unit 133 calculates the absolute value of the difference with respect to the gait parameter for both feet used for estimation of the waist swinging. Hereinafter, the absolute value of the difference is also referred to as a difference. The average value or difference regarding the first feature amount/gait parameter for both feet calculated by the calculation unit 133 is also referred to as a second feature amount. The second feature amount is used for estimation of waist swinging. Instead of the average value or difference of the first feature amount or the gait parameter included in the feature amount data generated by the measurement device 10, the first feature amount or the gait parameter may be directly used for estimation of the waist swinging. In this case, the calculation unit 133 can be omitted.

The storage unit 135 stores an estimation model for estimation of waist swinging. The estimation model outputs an estimation result regarding waist swinging according to an input of input data calculated by the calculation unit 133. The storage unit 135 stores estimation models learned for a plurality of subjects. In a case where the attribute of the subject is used for estimation, the storage unit 135 stores the attribute of the subject. For example, the attribute of the subject includes gender, age, body weight, height, and the like of the subject. The waist swinging estimation device 13 estimates waist swinging in three directions of the traveling direction, the left-right direction, and the vertical direction. The attribute of the subject varies depending on the direction of the waist swinging that is an estimation target.

The estimation model is stored in the storage unit 135 at timing of factory shipment of a product, calibration before the user uses the estimation system, or the like. For example, the estimation system 1 may be configured to use an estimation model stored in a storage device such as an external server. In that case, the estimation system 1 may be configured such that the estimation model is used via an interface (not illustrated) connected to the storage device.

The estimation unit 137 acquires, from the calculation unit 133, input data used for estimation of waist swinging. When the feature amount data generated by the measurement device 10 is used as it is, the estimation unit 137 acquires the feature amount data as input data. In a case where the attribute of the subject is used for estimation, the estimation unit 137 acquires the attribute of the subject from the storage unit 135.

The estimation unit 137 estimates waist swinging using the acquired input data. In the present example embodiment, an example will be described in which the fluctuation width of the waist swinging corresponding to the difference between the maximum value and the minimum value of the waist swinging in one gait cycle is estimated. The estimation unit 137 inputs input data to the estimation model stored in the storage unit 135. The estimation unit 137 outputs the estimation result of the waist swinging output from the estimation model. In a case where an estimation model stored in an external storage device constructed in a cloud, a server, or the like is used, the estimation unit 137 is configured to use the estimation model via an interface (not illustrated) connected to the storage device.

The waist swinging is an index indicating a relative waist position based on an average waist position of the subject during walking. The estimation unit 137 estimates waist swinging in three directions of the traveling direction, the left-right direction, and the vertical direction. By using the waist swinging, the movement of the subject, which cannot be grasped only by the movement of the foot, can be grasped.

Regarding waist swinging in the traveling direction, the front is positive, and the rear is negative. When the waist swinging in the traveling direction is positive, the waist position is located in front of the average waist position in the traveling direction. When the waist swinging in the traveling direction is negative, the waist position is located behind the average waist position in the traveling direction.

Figure 11:
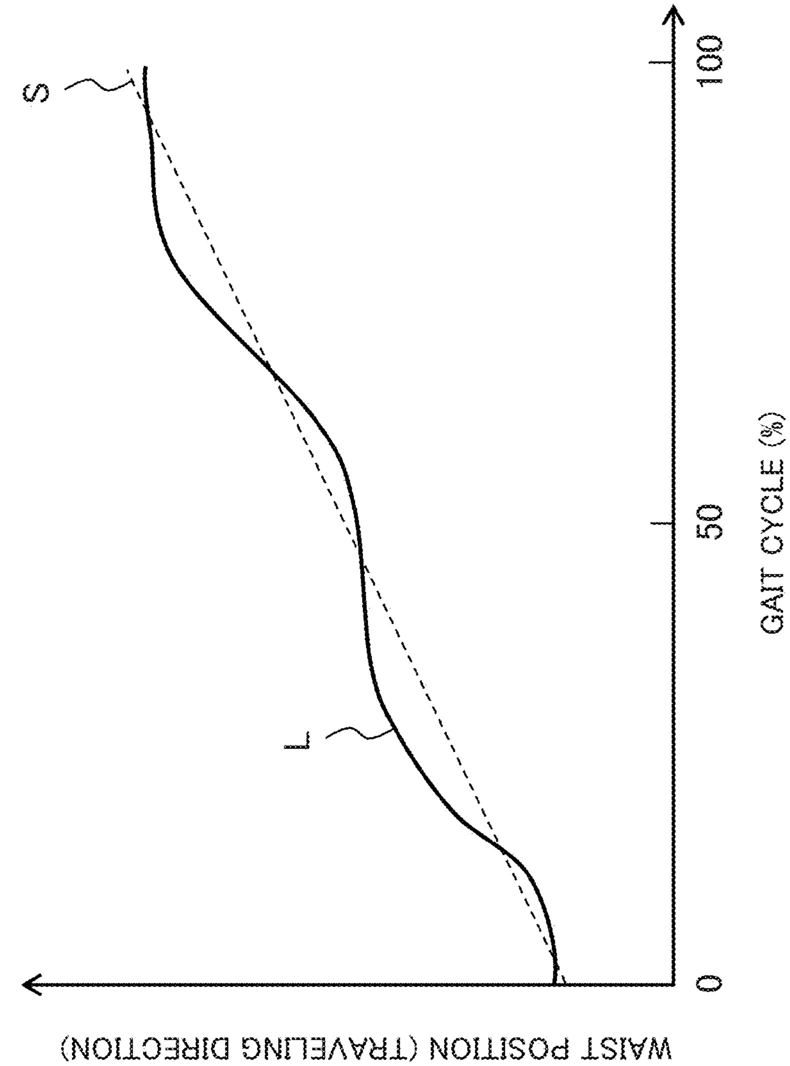
FIG. 11 is a graph illustrating an example of time-series data of a waist position in the traveling direction.
Figure 12:
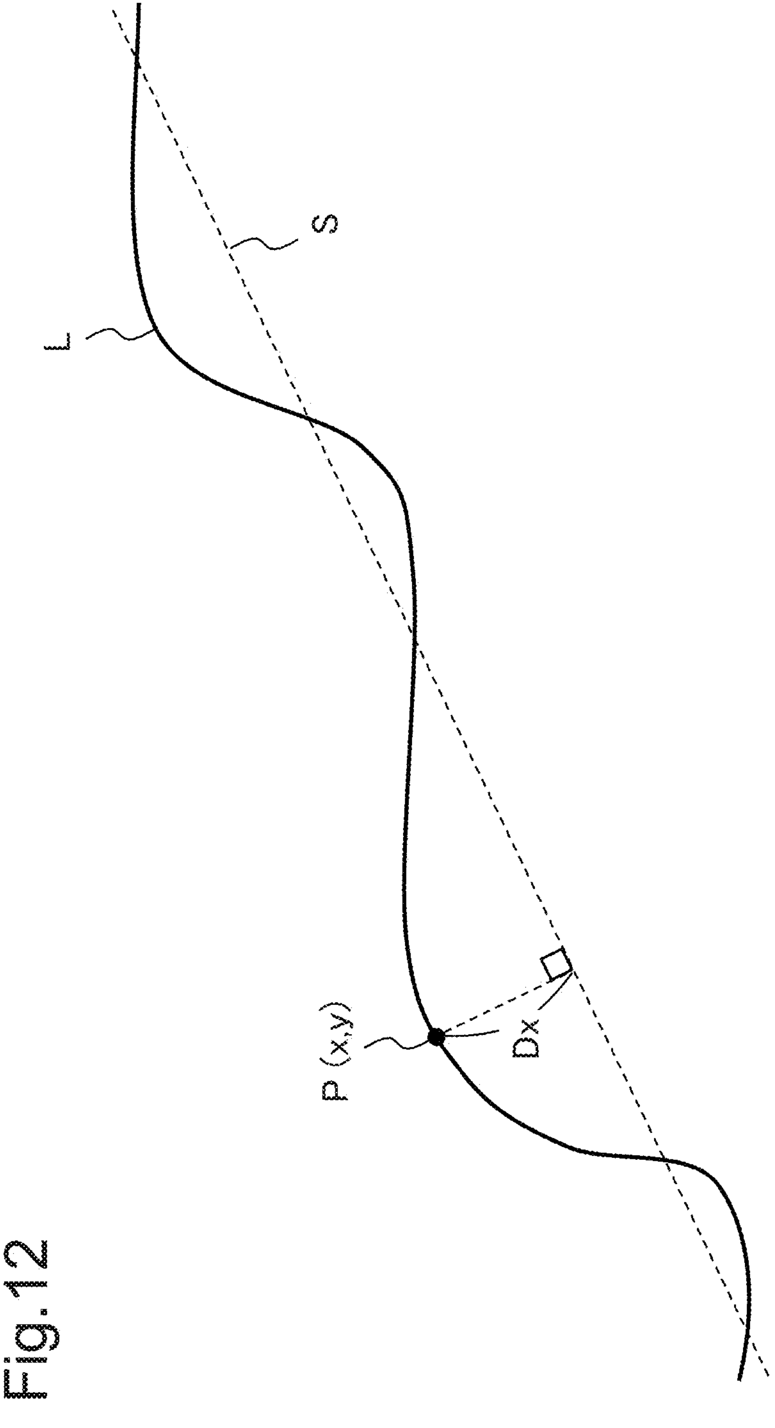
FIG. 12 is a graph for explaining a method of deriving waist swinging.

FIGS. 11 and 12 are graphs for explaining a method of deriving waist swinging in the traveling direction. FIG. 11 is a graph for explaining an example of time-series data of a waist position in the traveling direction. The graph of FIG. 11 illustrates time-series data L of the waist position in the traveling direction in one gait cycle. FIG. 11 illustrates a reference straight line S (broken line) obtained by approximating the time-series data L of the waist position in one gait cycle by a linear function. For example, the reference straight line S is a regression straight line of the time-series data L of the waist position in one gait cycle. The distance between each point of the time-series data L of the waist position in one gait cycle and the reference straight line S is waist swinging.

FIG. 12 is a conceptual diagram illustrating waist swinging in the graph of FIG. 11 in an emphasized manner. A point P(x, y) of the time-series data L of the waist position indicates the waist position in the gait phase x. The length of the perpendicular drawn from the point P(x, y) of the time-series data L of the waist position to the reference straight line S is the waist swinging Dx in the gait phase x. When the waist position of the subject is in front of the position of the subject according to the average speed in the predetermined gait section, the waist swinging Dx is positive. When the waist position of the subject is behind the position of the subject according to the average speed in the predetermined gait section, the waist swinging Dx is negative. The farther the waist position is from the position of the subject according to the average speed, the larger the absolute value of waist swinging Dx is. As the waist position is closer to the position of the subject according to the average speed, the absolute value of the waist swinging Dx is smaller.

Figure 13:
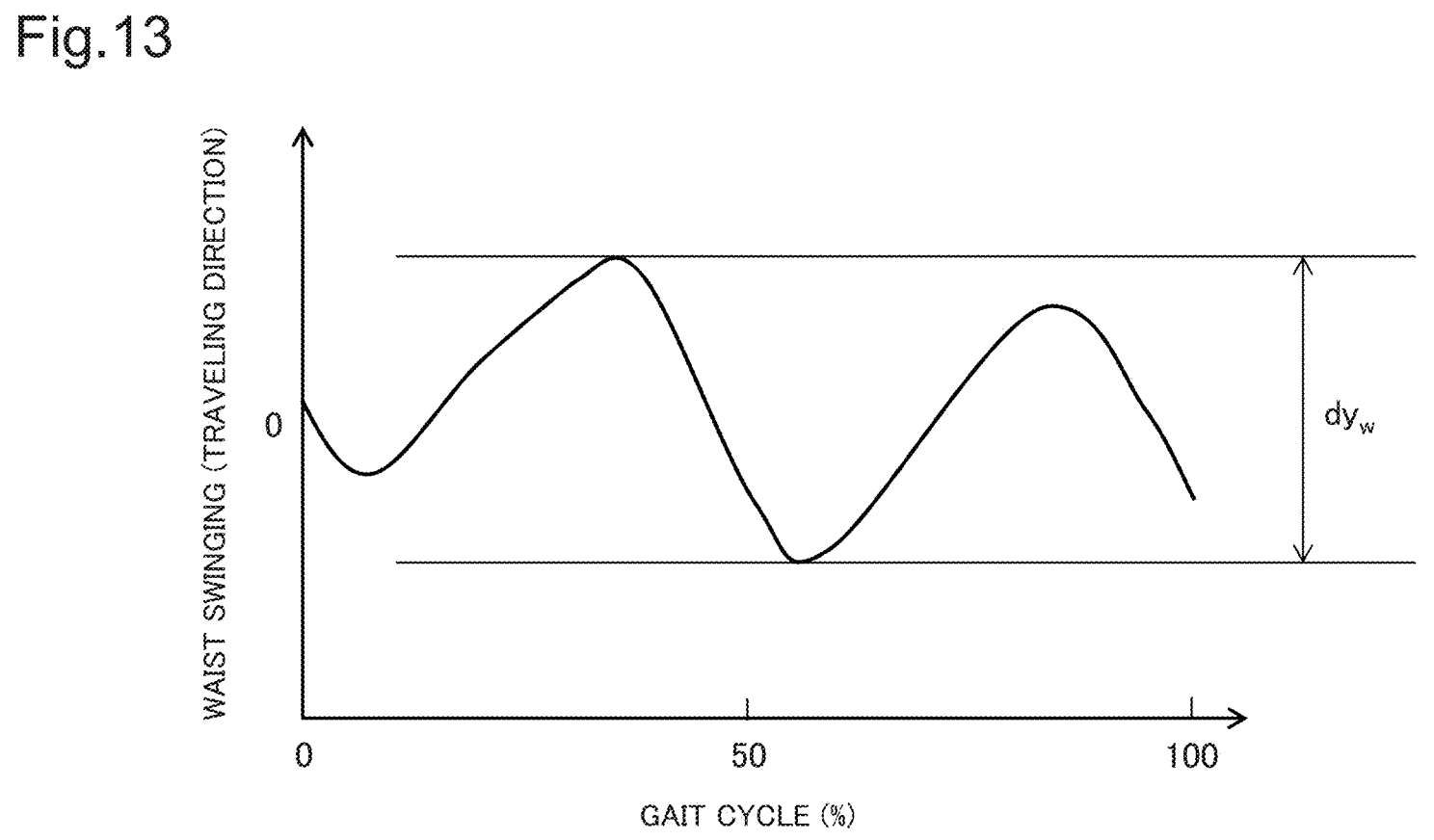

FIG. 13 is a graph illustrating an example of time-series data of waist swinging in the traveling direction. In the graph of FIG. 13, the time-series data of waist swinging in the traveling direction is associated with the gait cycle. In one gait cycle, a difference $dy_w$ between the maximum value and the minimum value of waist swinging in the traveling direction corresponds to a fluctuation width of the waist swinging in the traveling direction.

Regarding waist swinging in the left-right direction, either one of the left and right is positive, and the other is negative. For example, it is assumed that the left is positive and the right is negative. When the waist swinging in the left-right direction is positive, the waist position is located on the left side with respect to the gait route along the traveling direction of the subject. When the waist swinging in the left-right direction is negative, the waist position is located on the right side with respect to the gait route along the traveling direction of the subject.

Figure 14:
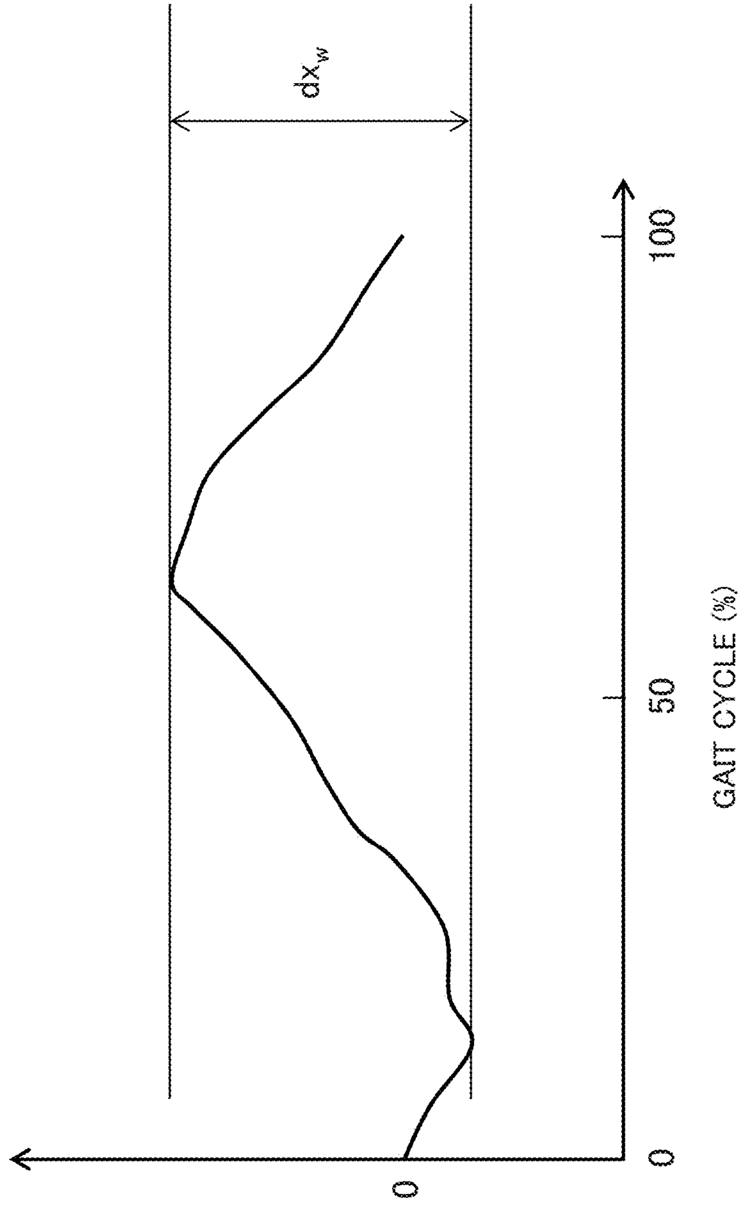
FIG. 14 is a graph for explaining an example of a difference in waist swinging in a left-right direction.

FIG. 14 is a graph illustrating an example of time-series data of waist swinging in the left-right direction. In the graph of FIG. 14, the time-series data of waist swinging in the left-right direction is associated with the gait cycle. In one gait cycle, a difference dx w between the maximum value and the minimum value of waist swinging in the left-right direction corresponds to a fluctuation width of waist swinging in the left-right direction.

Regarding waist swinging in the vertical direction, the upper side is positive and the lower side is negative. When the waist swinging in the vertical direction is positive, the waist position is located above the average waist position in the vertical direction. When the waist swinging in the vertical direction is negative, the waist position is located below the average waist position in the vertical direction.

Figure 15:
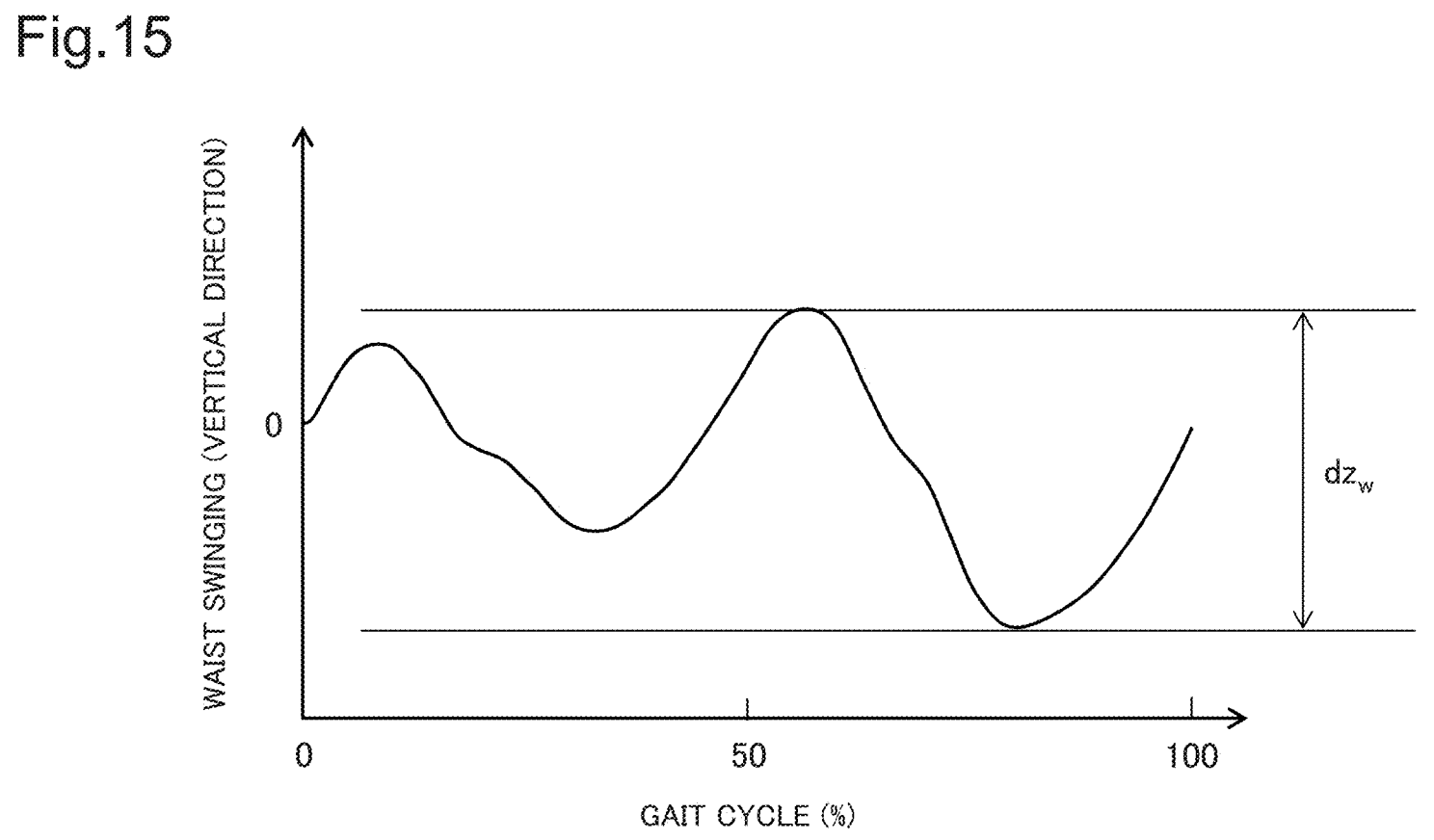

FIG. 15 is a graph illustrating an example of time-series data of waist swinging in the vertical direction. In the graph of FIG. 15, the time-series data of waist swinging in the vertical direction is associated with the gait cycle. In one gait cycle, a difference $dz_w$ between the maximum value and the minimum value of waist swinging in the vertical direction corresponds to a fluctuation width of waist swinging in the vertical direction.

Figure 16:
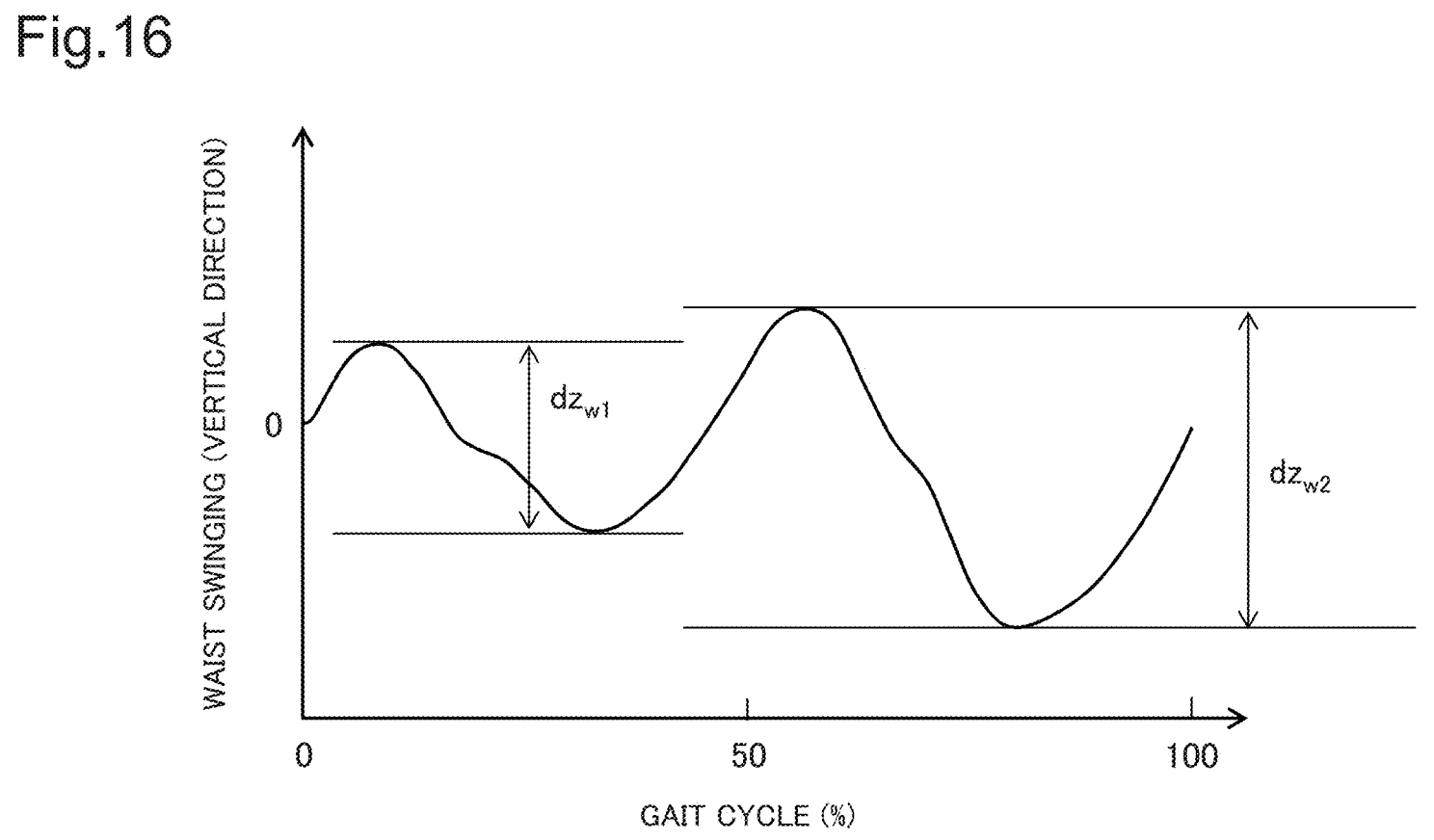

FIG. 16 is a graph illustrating another example of time-series data of waist swinging in the vertical direction. In the graph of FIG. 16, the time-series data of waist swinging in the vertical direction is associated with the gait cycle. Two amplitudes appear in the time-series data of the waist swinging in the vertical direction. In the example of FIG. 16, in one gait cycle, the fluctuation width (difference $dz_{w1}$) of the preceding amplitude and the fluctuation width (difference $dz_{w2}$) of the following amplitude are separately estimated. For example, the fluctuation width (difference $dz_{w1}$) of the preceding amplitude and the fluctuation width (difference $dz_{w2}$) of the following amplitude are estimated using different estimation models corresponding to the fluctuation width of the preceding amplitude and the fluctuation width of the following amplitude.

The output unit 139 outputs the estimation result of the waist swinging by the estimation unit 137. For example, the output unit 139 displays the estimation result of the waist swinging on the screen of the mobile terminal of a subject (user). For example, the output unit 139 outputs the estimation result to an external system or the like that uses the estimation result. The use of the information regarding the waist swinging output from the waist swinging estimation device 13 is not particularly limited.

For example, the waist swinging estimation device 13 is connected to an external system or the like constructed in a cloud or a server via a mobile terminal (not illustrated) carried by a subject (user). The mobile terminal (not illustrated) is a portable communication device. For example, the mobile terminal is a portable communication device having a communication function, such as a smartphone, a smart watch, or a mobile phone. For example, the waist swinging estimation device 13 is connected to the mobile terminal via a wire such as a cable. For example, the waist swinging estimation device 13 is connected to a mobile terminal via wireless communication. For example, the waist swinging estimation device 13 is connected to the mobile terminal via a wireless communication function (not illustrated) conforming to a standard such as Bluetooth (registered trademark) or WiFi (registered trademark). The communication function of the waist swinging estimation device 13 may conform to a standard other than Bluetooth (registered trademark) or WiFi (registered trademark). The estimation result of the waist swinging may be used by an application installed in the mobile terminal. In that case, the mobile terminal executes processing using the estimation result by application software or the like installed in the mobile terminal.

[Learning Example]

Next, a learning example of an estimation model used for estimation of waist swinging by the waist swinging estimation device 13 will be described with reference to a verification result regarding a correlation between a difference in waist swinging and feature amount data. Hereinafter, a verification example performed on 45 subjects will be described. In the following verification example, the correlation between the measured value and the estimated value of the waist swinging in gait is verified. In the present verification example, a subject wearing a smart apparel and a shoe on which the measurement device 10 is mounted has walked twice on a straight path of 5 m. An IMU that measures a spatial acceleration and a spatial angular velocity is mounted on a waist portion of the smart apparel. The measured values are derived using the measurement values of the spatial acceleration and the spatial angular velocity of the waist of the subject. The prediction value is an estimated value estimated using sensor data measured by the measurement device 10 mounted on the shoe worn by the subject at the same time as the measurement of the measured value. The correlation between the measured value and the estimated value is evaluated by a correlation coefficient.

Figure 17:
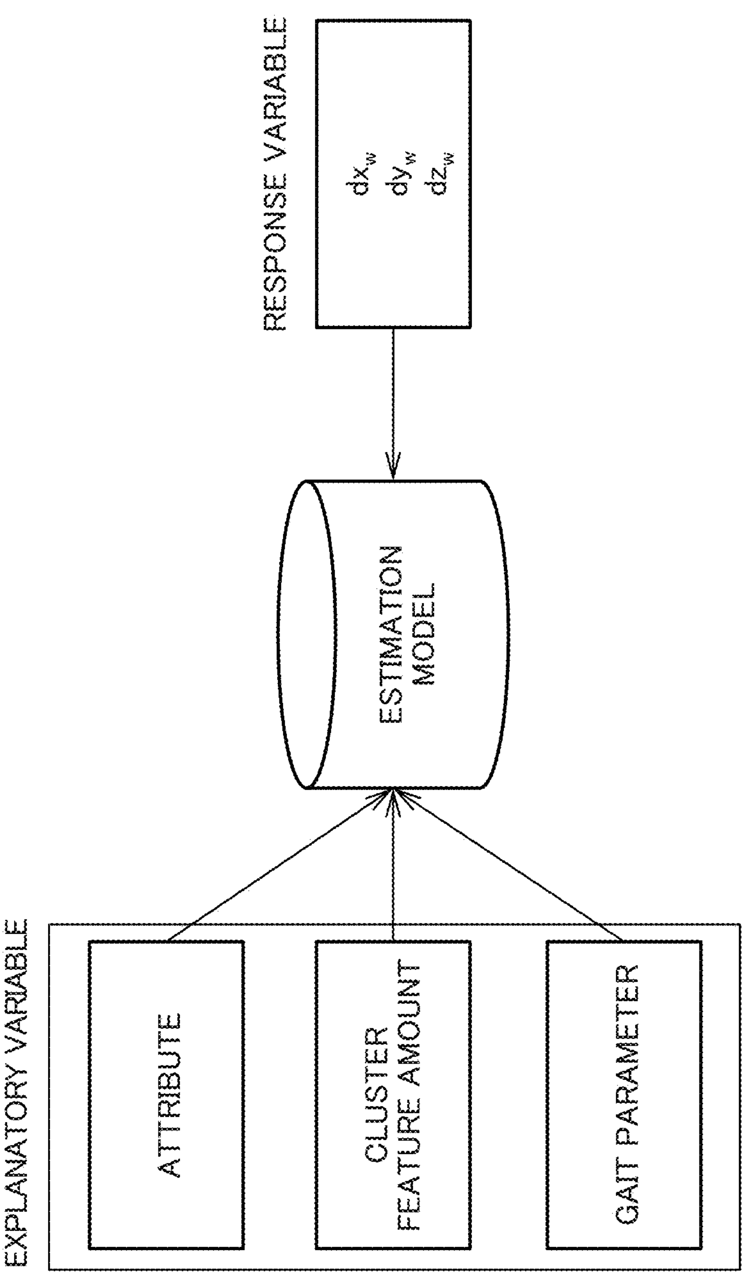
FIG. 17 is a conceptual diagram for explaining learning of an estimation model used by a waist swinging estimation device included in the estimation system according to the first example embodiment.

FIG. 17 is a conceptual diagram for explaining an example of learning of an estimation model used for estimation of waist swinging. For learning of the estimation model, explanatory variables and response variables regarding a plurality of subjects are used. As the explanatory variable, the attribute of the subject, the cluster feature amount generated according to the gait of the subject, and the gait parameter are used. As the response variable, a measured value of the fluctuation width of the waist swinging simultaneously measured at the time of measuring the sensor data for generating the cluster feature amount and the gait parameter is used. The measured value of the fluctuation width of the waist swinging includes a difference $dx_w$ in the traveling direction, a difference $dy_w$ in the left-right direction, and a difference $dz_w$ in the vertical direction. For example, the measured value of the fluctuation width of the waist swinging is derived using the measurement value measured by the IMU attached to the waist of the subject. For example, the estimation model is a multiple regression model constructed using the feature amount selected by the Leave-one-subject-out LASSO method.

For example, the estimation model is constructed by learning using a linear regression algorithm. For example, the estimation model is constructed by learning using an algorithm of a support vector machine (SVM). For example, the estimation model is constructed by learning using a Gaussian Process Regression (GPR) algorithm. For example, the estimation model is constructed by learning using a random forest (RF) algorithm. The estimation model may be constructed by unsupervised learning that classifies a subject who is a generation source of the feature amount data according to the feature amount data. The algorithm used for learning the estimation model is not particularly limited.

The estimation model may be constructed by learning using gait waveform data (sensor data) for one gait cycle as an explanatory variable. For example, the estimation model is constructed by supervised learning in which the acceleration in the three axial directions, the angular velocity around the three axial directions, and the gait waveform data of the angle (posture angle) around the three axial directions are used as explanatory variables, and the measured value of the fluctuation width of the waist swinging that is the estimation target is used as an objective variable.

<Traveling Direction>

The average value or difference of the first feature amount/gait parameter regarding both feet is used to estimate the difference in waist swinging in the traveling direction. The body weight is used as the attribute of the user to estimate the difference in waist swinging in the traveling direction.

FIG. 18 is a table summarizing a part of the second feature amounts regarding both feet used for estimation of the difference in waist swinging in the traveling direction. Regarding the estimation of the difference in waist swinging in the traveling direction, the average value of both feet regarding the acceleration $A_y$ in the traveling direction, an angular velocity $G_y$ around the traveling axis, and an angular velocity $G_z$ around the vertical axis is used as the second feature amount. Regarding the acceleration $A_y$ in the traveling direction, the second feature amount $F_{y1}$ in the section of the gait phase 92 to 94% is used for estimation. Regarding the angular velocity $G_y$ around the traveling axis, the second feature amount $F_{y2}$ in the section of the gait phase 76 to 81% is used for estimation. Regarding the angular velocity $G_z$ around the vertical axis, the second feature amount $F_{y3}$ in the section of the gait phase 92% is used for estimation. Regarding the estimation of the difference in waist swinging in the traveling direction, the difference between both legs with respect to the angular velocity $G_y$ around the traveling axis and the angular velocity $G_z$ around the vertical axis is used as the second feature amount. Regarding the angular velocity $G_y$ around the traveling axis, the second feature amount $F_{y4}$ in the section of the gait phase 91 to 92% is used for estimation. Regarding the angular velocity $G_z$ around the vertical axis, the second feature amount $F_{y5}$ in the section of the gait phase 3% is used for estimation.

A plurality of gait parameters are used to estimate a difference in waist swinging in the traveling direction. For example, an average value of both feet regarding the maximum dorsiflexion angle, the maximum dividing amount, the maximum toe height, the swing time, and the sole contact time is used as the second feature amount. For example, a difference between both feet regarding the roll angle during toe off, the standing time, the sole contact time, the swing minimum value, and the maximum speed during swinging is used as the second feature amount. In this verification, regarding the estimation of the difference in waist swinging in the traveling direction, the correlation coefficient between the measured value and the estimated value has been 0.6957.

<Left-Right Direction>

The average value or difference of the first feature amount/gait parameter regarding both feet is used to estimate the difference in waist swinging in the left-right direction. The height is used as the attribute of the user in estimating the difference in waist swinging in the left-right direction.

FIG. 19 is a table summarizing a part of the second feature amounts regarding both feet used for estimation of a difference in waist swinging in the left-right direction. Regarding the estimation of the difference in waist swinging in the left-right direction, the average value of both feet with respect to the acceleration $A_y$ in the traveling direction is used as the second feature amount. Regarding the acceleration $A_y$ in the traveling direction, the second feature amount $F_{x1}$ in the section of the gait phase 62% is used for estimation. Regarding the estimation of the difference in waist swinging in the left-right direction, the difference between both legs with respect to the angle (pitch angle) $E_y$ around the traveling axis is used as the second feature amount. Regarding the angle (pitch angle) $E_y$ around the traveling axis, the second feature amount $F_{x2}$ in the section of the gait phase 79 to 81% is used for estimation.

A plurality of gait parameters are used to estimate a difference in waist swinging in the left-right direction. For example, the average value of both feet regarding the gait speed, the maximum dorsiflexion angle, the maximum toe height, the in-and-out inversion angle, the roll angle during heel contact, the swing time, the load time, the sole contact time, DST2, the swing peak, the maximum speed during swinging, and the maximum foot-rising acceleration during swinging is used as the second feature amount. For example, a difference between both feet regarding a stride, a gait speed, a maximum dorsiflexion angle, a maximum dividing amount, a roll angle during toe off, a swing time, a load time, a kicking time, DST2, a swing minimum value, a swinging peak, and a foot-rising maximum acceleration during swinging is used as the second feature amount. In this verification, regarding the estimation of the difference in waist swinging in the left-right direction, the correlation coefficient between the measured value and the estimated value has been 0.7765.

<Vertical Direction>

The average value or difference of the first feature amount/gait parameter regarding both feet is used to estimate the difference in waist swinging in the vertical direction. Age and body weight are used as attributes of the user to estimate the difference in waist swinging in the vertical direction. In the present example embodiment, an example in which the first feature amount is not used will be described.

A plurality of gait parameters are used to estimate a difference in waist swinging in the vertical direction. For example, an average value of both feet regarding the stride length, the maximum dorsiflexion angle, the roll angle during toe off, the load time, the kicking time, and DST2 is used as the second feature amount. For example, a difference between both feet regarding the maximum dorsiflexion angle, the swing time, the swing peak, and the maximum speed during swing is used as the second feature amount. In this verification, regarding the estimation of the difference in waist swinging in the traveling direction, the correlation coefficient between the measured value and the estimated value has been 0.3669.

Regarding the estimation of the difference in waist swinging in the vertical direction, as illustrated in FIG. 16, there is also an example in which the difference $dz_{w1}$ of the preceding amplitude and the difference $dz_{w2}$ of the following amplitude are separately estimated in one gait cycle. In this case, regarding the preceding amplitude difference $dz_{w1}$, the correlation coefficient between the measured value and the estimated value has been 0.4838. Regarding the difference $dz_{w2}$ of the subsequent amplitude, the correlation coefficient between the measured value and the estimated value has been 0.4819. As described above, regarding the estimation of the difference in waist swinging in the vertical direction, the correlation coefficient has been larger when the difference $dz_{w1}$ of the preceding amplitude and the difference $dz_{w2}$ of the subsequent amplitude have been separately estimated.

(Operation)

Next, an operation of the estimation system 1 will be described with reference to the drawings. Here, the measurement device 10 and the waist swinging estimation device 13 included in the estimation system 1 will be individually described. Regarding the measurement device 10, the operation of the feature-amount-data generation unit 12 included in the measurement device 10 will be described.

[Measurement Device]

Figure 20:
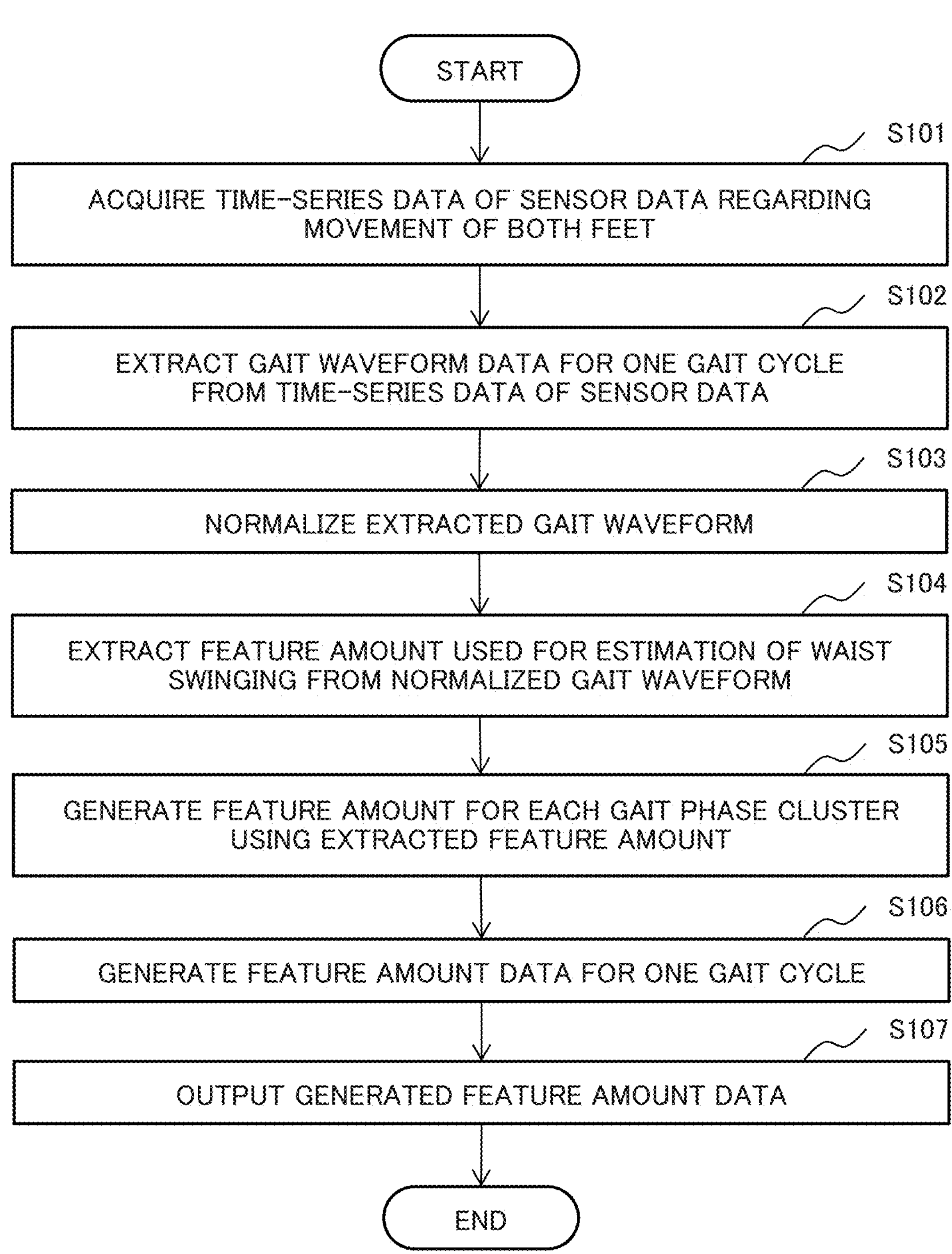
FIG. 20 is a flowchart for explaining an example of the operation of the measurement device included in the estimation system according to the first example embodiment.

FIG. 20 is a flowchart for explaining the operation of the feature-amount-data generation unit 12 included in the measurement device 10. In the description along the flowchart of FIG. 20, the feature-amount-data generation unit 12 will be described as an operation subject.

In FIG. 20, first, the feature-amount-data generation unit 12 acquires time-series data of sensor data regarding the movement of both feet (step S101).

Next, the feature-amount-data generation unit 12 extracts gait waveform data for one gait cycle from the time-series data of the sensor data (step S102). The feature-amount-data generation unit 12 detects the heel contact and the toe off from the time-series data of the sensor data. The feature-amount-data generation unit 12 extracts time-series data of a section between consecutive heel contacts as gait waveform data for one gait cycle.

Next, the feature-amount-data generation unit 12 normalizes the extracted gait waveform data for one gait cycle (step S103). The feature-amount-data generation unit 12 normalizes the gait waveform data for one gait cycle to a gait cycle of 0 to 100% (first normalization). Further, the feature-amount-data generation unit 12 normalizes the ratio of the stance phase to the swing phase in the first-normalized gait waveform data for one gait cycle to 60:40 (second normalization).

Next, the feature-amount-data generation unit 12 extracts a feature amount from a gait phase used for estimation of waist swinging with respect to the normalized gait waveform (step S104). The feature-amount-data generation unit 12 extracts a feature amount used for estimation of waist swinging.

Next, the feature-amount-data generation unit 12 generates a cluster feature amount (first feature amount) for each gait phase cluster using the extracted feature amount (step S105). In a case where the gait parameter is used in the estimation of the waist swinging, the feature-amount-data generation unit 12 generates the gait parameter.

Next, the feature-amount-data generation unit 12 integrates the cluster feature amounts for each gait phase cluster to generate feature amount data for one gait cycle (step S106).

Next, the feature-amount-data generation unit 12 outputs the generated feature amount data to the waist swinging estimation device 13 (step S107).

[Waist Swinging Estimation Device]

FIG. 21 is a flowchart for explaining the operation of the waist swinging estimation device 13. In the description along the flowchart of FIG. 21, the waist swinging estimation device 13 will be described as an operation subject.

In FIG. 21, first, the waist swinging estimation device 13 acquires feature amount data used for estimation of waist swinging from the measurement device 10 (step S131).

Next, the waist swinging estimation device 13 calculates the average value of the first feature amounts included in the acquired feature amount data and the absolute value of the difference as the second feature amount (step S132).

Next, the waist swinging estimation device 13 inputs input data including the calculated second feature amount to an estimation model that estimates waist swinging (step S133).

Next, the waist swinging estimation device 13 estimates the waist swinging of the user according to the output (estimated value) from the estimation model (step S134). For example, the waist swinging estimation device 13 estimates a difference in waist swinging of the user as the waist swinging of the user.

Next, the waist swinging estimation device 13 outputs information according to the estimated waist swinging (step S135). For example, the waist swinging is output to a terminal device (not illustrated) carried by the user. For example, the information according to waist swinging is output to a system that executes processing using the information.

(Application Example)

Next, an application example according to the present example embodiment will be described with reference to the drawings. In the following application example, an example in which the function of the waist swinging estimation device 13 installed in the mobile terminal carried by the user estimates the information on the waist swinging using the feature amount data measured by the measurement device 10 arranged in the shoe will be described.

Figure 22:
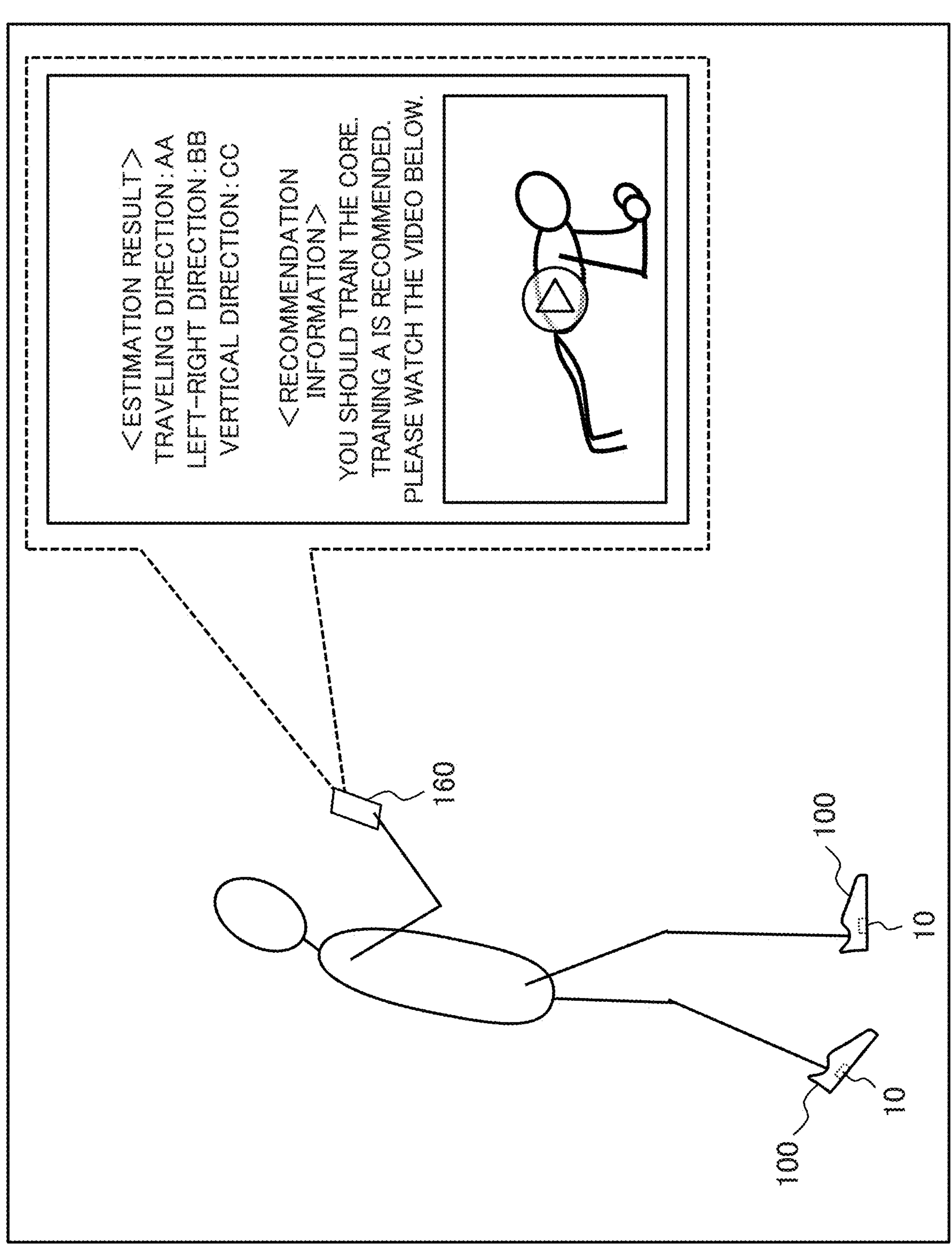
FIG. 22 is a conceptual diagram for explaining an application example of the estimation system according to the first example embodiment.
Figure 23:
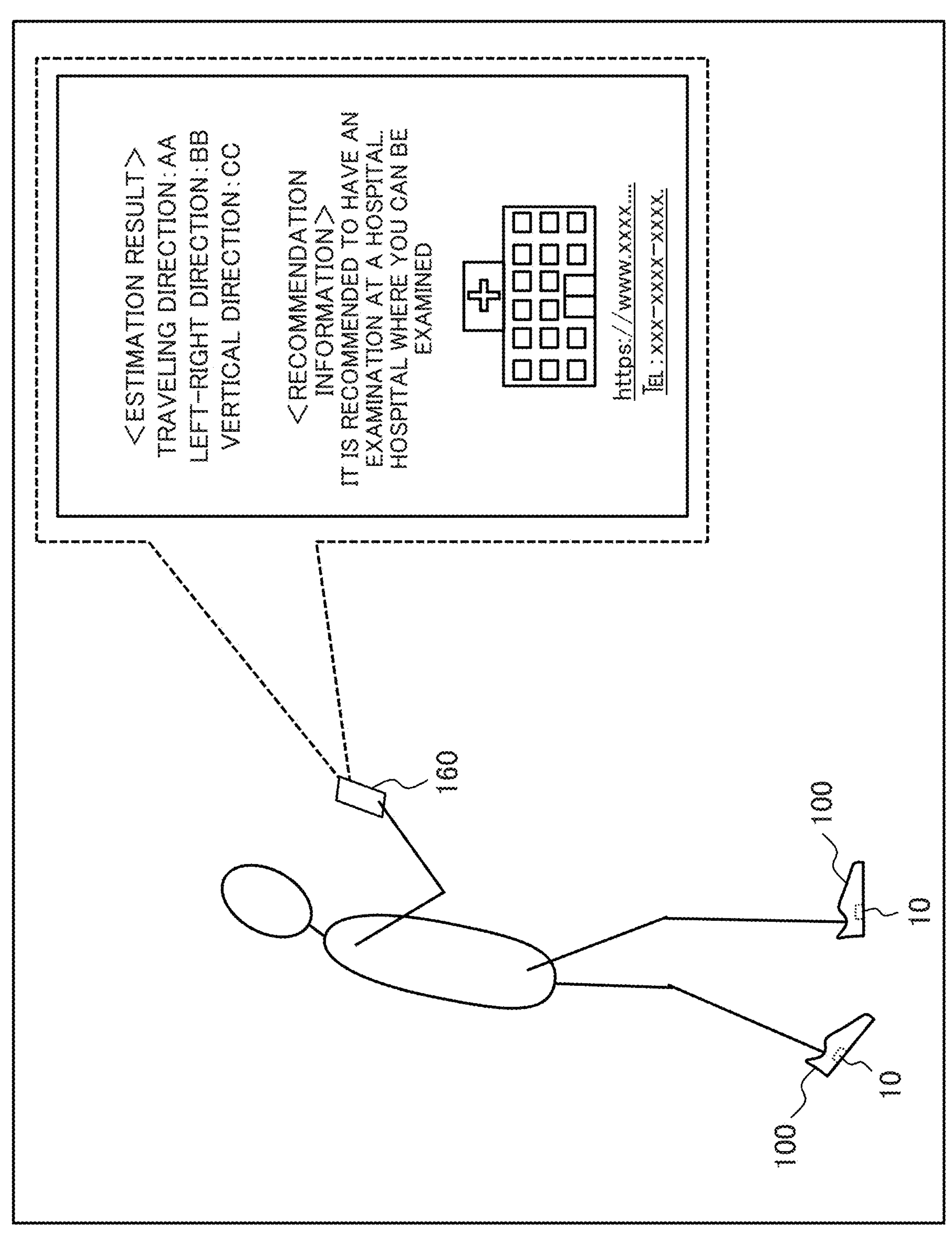
FIG. 23 is a conceptual diagram for explaining an application example of the estimation system according to the first example embodiment.

FIGS. 22 and 23 are conceptual diagrams illustrating an example of displaying the estimation result by the waist swinging estimation device 13 on a screen of a mobile terminal 160 carried by the user walking while wearing the shoes 100 on which the measurement device 10 is disposed. In the examples of FIGS. 22 and 23, information according to the estimation result of the waist swinging using the feature amount data according to the sensor data measured while the user is walking is displayed on the screen of the mobile terminal 160.

In the example of FIG. 22, an estimation result of waist swinging in the traveling direction, the left-right direction, and the vertical direction is displayed on the display unit of the mobile terminal 160. In the example of FIG. 22, recommendation information according to the estimation result of the waist swinging of "It is better to train the core." is displayed on the display unit of the mobile terminal 160 according to the estimated value of the waist swinging. In the example of FIG. 22, in accordance with the estimated value of the waist swinging, that recommendation information according to the estimation result like "Training A is recommended. Please watch the video below." is displayed on the display unit of the mobile terminal 160. The user who has confirmed the information displayed on the display unit of the mobile terminal 160 can practice for training the core by exercising with reference to the video of the training A according to the recommendation information.

In the example of FIG. 23, an estimation result of waist swinging in the traveling direction, the left-right direction, and the vertical direction is displayed on the display unit of the mobile terminal 160. In the example of FIG. 23, recommendation information of "It is recommended to have an examination at a hospital." is displayed on the display unit of the mobile terminal 160 according to the estimated value of waist swinging. For example, a link destination or a telephone number to a hospital site that can be examined may be displayed on the screen of the mobile terminal 160. The user who has confirmed the information displayed on the display unit of the mobile terminal 160 can appropriately receive an examination of a disease regarding the knee by going to a hospital according to the recommendation information.

As described above, the estimation system of the present example embodiment includes the measurement device and the waist swinging estimation device. The measurement device is installed on footwear of a subject who is an estimation target of waist swinging which is an index regarding movement of the waist. The measurement device includes a sensor and a feature-amount-data generation unit. The sensor measures a spatial acceleration and a spatial angular velocity. The sensor generates sensor data regarding the movement of the foot using the measured spatial acceleration and spatial angular velocity. The sensor outputs the generated sensor data. The feature-amount-data generation unit acquires time-series data of sensor data including a feature of a gait. The feature-amount-data generation unit extracts gait waveform data for one gait cycle from the time-series data of the sensor data. The feature-amount-data generation unit normalizes the extracted gait waveform data. The feature-amount-data generation unit extracts, based on the normalized gait waveform data, a feature amount used for estimation of waist swinging from a gait phase cluster configured by at least one temporally continuous gait phase. The feature-amount-data generation unit generates feature amount data including the extracted feature amount. The feature-amount-data generation unit outputs the generated feature amount data to the waist swinging estimation device.

The waist swinging estimation device includes a communication unit, a storage unit, an estimation unit, and an output unit. The communication unit acquires feature amount data including a feature amount extracted from the gait waveforms of the spatial acceleration and the spatial angular velocity included in the sensor data regarding the movement of the foot of the subject and used for estimation of waist swinging that is an index regarding the movement of the waist. The storage unit stores an estimation model that outputs an estimated value regarding waist swinging according to an input of a feature amount included in the feature amount data. The estimation unit inputs the feature amount included in the acquired feature amount data to the estimation model, and estimates the waist swinging of the subject according to the estimated value regarding the waist swinging output from the estimation model. The output unit outputs information according to the waist swinging of the subject.

In the present example embodiment, by using the feature amount extracted from the sensor data regarding the movement of the foot of the subject, the waist swinging that is an index regarding the movement of the waist of the subject is estimated. Therefore, according to the present example embodiment, in daily life, waist swinging that is an index regarding the movement of the waist can be easily estimated with high accuracy.

In one aspect of the present example embodiment, the communication unit acquires feature amount data including a gait parameter extracted from gait waveforms of a spatial acceleration and a spatial angular velocity included in sensor data. The storage unit stores an estimation model that outputs an estimated value regarding waist swinging according to an input of a gait parameter included in the feature amount data. The estimation unit inputs the gait parameter included in the acquired feature amount data to the estimation model, and estimates the waist swinging of the subject according to the estimated value regarding the waist swinging output from the estimation model. According to the present aspect, the waist swinging can be estimated with high accuracy by using the feature amount data including the gait parameter.

In one aspect of the present example embodiment, the communication unit acquires the feature amount data including the first feature amount for each gait phase cluster extracted from the gait waveforms of the spatial acceleration and the spatial angular velocity included in the sensor data. The storage unit stores an estimation model that outputs an estimated value regarding waist swinging according to an input of a first feature amount included in the feature amount data. The estimation unit inputs the first feature amount included in the acquired feature amount data to the estimation model, and estimates the waist swinging of the subject according to the estimated value regarding the waist swinging output from the estimation model. According to the present aspect, the waist swinging can be estimated with higher accuracy by using the feature amount data including the first feature amount for each gait phase cluster.

A waist swinging estimation device according to an aspect of the present example embodiment includes a calculation unit. The calculation unit calculates, as the second feature amount, an average value and a difference regarding the first feature amount and the gait parameter used for estimation of the waist swinging among the first feature amount and the gait parameter for both feet of the subject. The storage unit stores an estimation model that outputs an estimated value regarding waist swinging according to the input of the second feature amount. The estimation unit inputs the calculated second feature amount to the estimation model, and estimates the waist swinging of the subject according to the estimated value regarding the waist swinging output from the estimation model. According to the present aspect, the waist swinging can be estimated with higher accuracy by using the average value/difference of the feature amounts for both feet.

In one aspect of the present example embodiment, the storage unit stores an estimation model that outputs an estimated value regarding waist swinging according to the input of the attribute of the subject and the second feature amount. The estimation unit inputs the attribute and the second feature amount of the subject to the estimation model, and estimates the waist swinging of the subject according to the estimated value regarding the waist swinging output from the estimation model. According to the present aspect, the waist swinging can be estimated with higher accuracy by using the attribute of the subject.

In one aspect of the present example embodiment, the storage unit stores an estimation model that outputs a fluctuation width of waist swinging in three directions of a traveling direction, a left-right direction, and a vertical direction in one gait cycle as an estimated value regarding the waist swinging according to an input of a feature amount included in the feature amount data. The estimation unit inputs the feature amount included in the acquired feature amount data to the estimation model, and estimates the waist swinging of the subject according to the fluctuation width of at least one of the waist swinging in three directions of the traveling direction, the left-right direction, and the vertical direction output from the estimation model. According to the present aspect, the waist swinging can be estimated with higher accuracy according to the fluctuation width of the waist swinging in the three directions of the traveling direction, the left-right direction, and the vertical direction.

In one aspect of the present example embodiment, the waist swinging estimation device is mounted on a terminal device having a screen visually recognizable by the subject. The waist swinging estimation device displays information regarding the waist swinging estimated according to the movement of the feet of the subject on the screen of the terminal device. According to the present aspect, the information regarding the waist swinging estimated for the subject can be accurately presented to the subject.

The waist swinging becomes an index of the physical condition and the health condition around the waist. For example, the waist swinging in the left-right direction is related to the left-right balance in gait. Therefore, waist swinging in the left-right direction is an index of gait stability. For example, if the user cannot walk in a flexible gait posture due to knee arthropathy, a sinking pattern of the body immediately after the foot lands becomes uncomfortable, and the waist swinging in the vertical direction is affected. Therefore, the waist swinging in the vertical direction becomes an index of the state and progress of knee arthropathy. For example, if there is hemiplegia, the body sinks down and the waist swinging in the vertical direction is affected at the timing of landing with the foot on the side of the half body to which the force is not applied. Therefore, the waist swinging in the vertical direction becomes an index of the state or progress of hemiplegia. For example, symptoms such as lumbar spinal stenosis, neurogenic intermittent claudication, and degenerative lumbar spondylolisthesis are also associated with waist swinging.

Second Example Embodiment

Next, a waist swinging estimation device according to a second example embodiment will be described with reference to the drawings. The waist swinging estimation device of the present example embodiment has a configuration in which the waist swinging estimation device of the first example embodiment is simplified.

Figure 24:
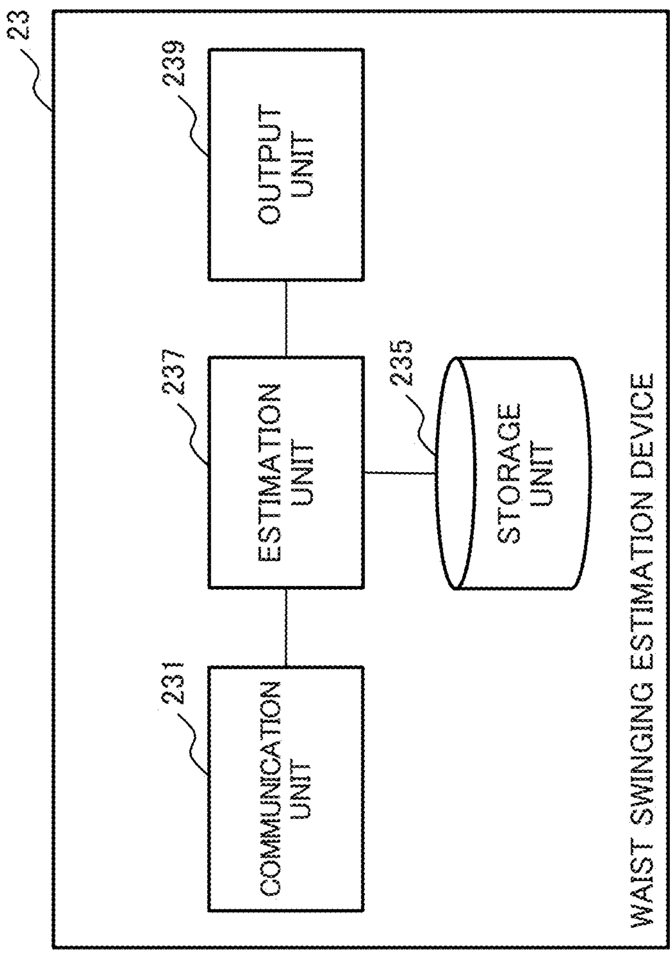
FIG. 24 is a block diagram illustrating an example of a configuration of a waist swinging estimation device according to a second example embodiment.

FIG. 24 is a block diagram illustrating an example of a configuration of a waist swinging estimation device 23 according to the present example embodiment. The waist swinging estimation device 23 includes a communication unit 231, a storage unit 235, an estimation unit 237, and an output unit 239.

The communication unit 231 acquires feature amount data including a feature amount extracted from the gait waveforms of the spatial acceleration and the spatial angular velocity included in the sensor data regarding the movement of the foot of the subject and used for estimation of waist swinging that is an index regarding the movement of the waist. The storage unit 235 stores an estimation model that outputs an estimated value regarding waist swinging according to an input of a feature amount included in the feature amount data. The estimation unit 237 inputs the feature amount included in the acquired feature amount data to the estimation model, and estimates the waist swinging of the subject according to the estimated value regarding the waist swinging output from the estimation model. The output unit 239 outputs information according to the waist swinging of the subject.

In the present example embodiment, by using the feature amount extracted from the sensor data regarding the movement of the foot of the subject, the waist swinging that is an index regarding the movement of the waist of the subject is estimated. Therefore, according to the present example embodiment, in daily life, waist swinging that is an index regarding the movement of the waist can be easily estimated with high accuracy.

(Hardware)

Here, a hardware configuration for executing the processing according to each example embodiment of the present disclosure will be described using an information processing device 90 (computer) of FIG. 25 as an example. The information processing device 90 in FIG. 25 is a configuration example for executing the processing of each example embodiment, and does not limit the scope of the present disclosure.

Figure 25:
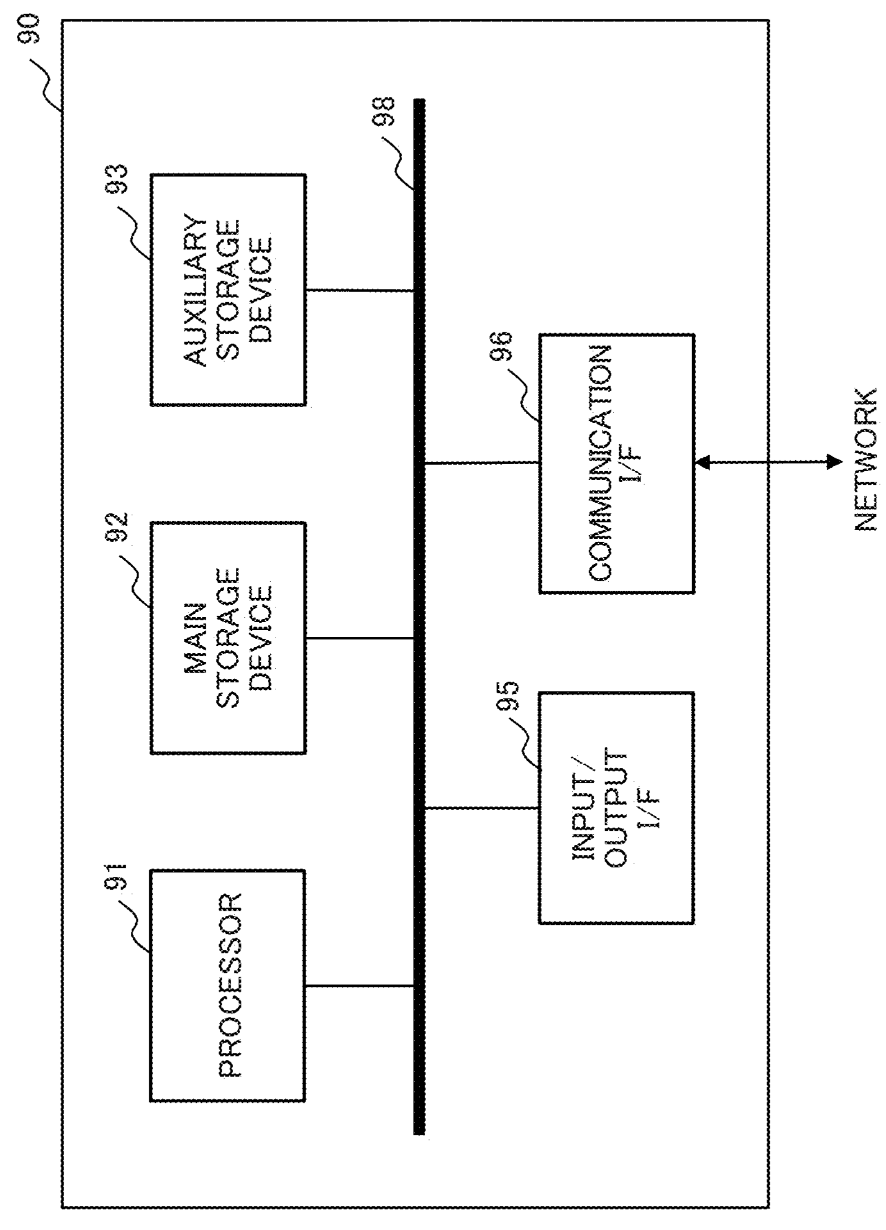
FIG. 25 is a block diagram illustrating an example of a hardware configuration that executes processing of each example embodiment.

As illustrated in FIG. 25, the information processing device 90 includes a processor 91, a main storage device 92, an auxiliary storage device 93, an input/output interface 95, and a communication interface 96. In FIG. 25, the interface is abbreviated as an I/F. The processor 91, the main storage device 92, the auxiliary storage device 93, the input/output interface 95, and the communication interface 96 are data-communicably connected to each other via a bus 98. The processor 91, the main storage device 92, the auxiliary storage device 93, and the input/output interface 95 are connected to a network such as the Internet or an intranet via the communication interface 96.

The processor 91 develops a program (instruction) stored in the auxiliary storage device 93 or the like in the main storage device 92. For example, the program is a software program for executing the processing of each example embodiment. The processor 91 executes the program developed in the main storage device 92. The processor 91 executes the processing according to each example embodiment by executing the program.

The main storage device 92 has a region in which a program is developed. A program stored in the auxiliary storage device 93 or the like is developed in the main storage device 92 by the processor 91. The main storage device 92 is implemented by, for example, a volatile memory such as a dynamic random access memory (DRAM). A nonvolatile memory such as a magneto resistive random access memory (MRAM) may be configured and added as the main storage device 92.

The auxiliary storage device 93 stores various data such as programs. The auxiliary storage device 93 is implemented by a local disk such as a hard disk or a flash memory. Various data may be stored in the main storage device 92, and the auxiliary storage device 93 may be omitted.

The input/output interface 95 is an interface for connecting the information processing device 90 and a peripheral device. The communication interface 96 is an interface for connecting to an external system or device through a network such as the Internet or an intranet based on a standard or a specification. The input/output interface and the communication interface 96 may be shared as an interface connected to an external device.

An input device such as a keyboard, a mouse, or a touch panel may be connected to the information processing device 90 as necessary. These input devices are used to input information and settings. When a touch panel is used as the input device, a screen having a touch panel function serves as an interface. The processor 91 and the input device are connected via the input/output interface 95.

The information processing device 90 may be provided with a display device for displaying information. In a case where a display device is provided, the information processing device 90 may include a display control device (not illustrated) for controlling display of the display device. The display device may be connected to the information processing device 90 via the input/output interface 95.

The information processing device 90 may be provided with a drive device. The drive device mediates reading of data and a program stored in a recording medium and writing of a processing result of the information processing device 90 to the recording medium between the processor 91 and the recording medium (program recording medium). The information processing device 90 and the drive device are connected via an input/output interface 95.

The above is an example of the hardware configuration for enabling the processing according to each example embodiment of the present invention. The hardware configuration of FIG. 25 is an example of a hardware configuration for executing the processing of each example embodiment, and does not limit the scope of the present invention. A program for causing a computer to execute processing according to each example embodiment is also included in the scope of the present invention.

Further, a program recording medium in which the program according to each example embodiment is recorded is also included in the scope of the present invention. The recording medium can be implemented by, for example, an optical recording medium such as a compact disc (CD) or a digital versatile disc (DVD). The recording medium may be implemented by a semiconductor recording medium such as a universal serial bus (USB) memory or a secure digital (SD) card. The recording medium may be implemented by a magnetic recording medium such as a flexible disk, or another recording medium. When a program executed by the processor is recorded in a recording medium, the recording medium is associated to a program recording medium.

The components of each example embodiment may be arbitrarily combined. The components of each example embodiment may be implemented by software. The components of each example embodiment may be implemented by a circuit.

The previous description of embodiments is provided to enable a person skilled in the art to make and use the present invention. Moreover, various modifications to these example embodiments will be readily apparent to those skilled in the art, and the generic principles and specific examples defined herein may be applied to other embodiments without the use of inventive faculty. Therefore, the present invention is not intended to be limited to the example embodiments described herein but is to be accorded the widest scope as defined by the limitations of the claims and equivalents.

Further, it is noted that the inventor's intent is to retain all equivalents of the claimed invention even if the claims are amended during prosecution.

What is claimed is:

1. A waist swinging estimation device comprising:

at least one memory storing instructions; and at least one processor connected to the at least one memory and configured to execute the instructions to:

acquire, via a communication interface, feature-amount data generated by a measurement device mounted on footwear of the subject in a position corresponding to an arch of the subject, the feature-amount data being produced from time-series sensor data of spatial accelerations and spatial angular velocities measured by a sensor installed on footwear of left and right feet by (i) detecting heel-contact and toe-off gait events, (ii) first normalizing one gait cycle to 0-100%, (iii) second normalizing a stance/swing ratio to 60/40, and (iv) extracting first feature amounts from a gait-phase cluster selected by correlation analysis;

calculate second feature amounts as bilateral statistics including an average value and an absolute difference of at least the first feature amounts and gait parameters for both feet, and input the second feature amounts together with one or more subject attributes to an estimation model;

estimate the waist swinging of the subject according to an output of the estimation model; and output information according to waist swinging of the subject including the fluctuation width and feedback information for gait correction;

wherein the estimation model is a trained machine-learning model learned using, for a plurality of subjects, an attribute of the subject, a cluster feature amount generated according to a gait of the subject, and a gait parameter, is trained to correlate foot-movement patterns with waist-movement characteristics, and is configured to output, for one gait cycle, a fluctuation width of waist swinging in at least one of a traveling direction, a left-right direction, and a vertical direction, the fluctuation width being defined as a difference between a maximum and a minimum of perpendicular distances from a regression line of a waist-position time series over one gait cycle detected by heel-contact and toe-off events.

2. The waist swinging estimation device according to claim 1, wherein:

the estimation model is configured to output an estimated value regarding the waist swinging according to an input of a gait parameter included in the feature amount data in addition to the second feature amounts, and the at least one processor is configured to execute the instructions to:

acquire the feature amount data including a gait parameter extracted from a gait waveform of the spatial acceleration and the spatial angular velocity included in the sensor data;

input the gait parameter included in the acquired feature amount data to the estimation model in addition to the second feature amounts; and estimate waist swinging of the subject according to the estimated value regarding the waist swinging output from the estimation model.

3. The waist swinging estimation device according to claim 2, wherein:

the estimation model is configured to output an estimated value regarding the waist swinging according to an input of the first feature amount included in the feature amount data in addition to the second feature amounts, and the at least one processor is configured to execute the instructions to:

acquire the feature amount data including a first feature amount for each gait phase cluster extracted from a gait waveform of a spatial acceleration and a spatial angular velocity included in the sensor data;

input the first feature amount included in the acquired feature amount data to the estimation model in addition to the second feature amounts; and estimate waist swinging of the subject according to the estimated value regarding the waist swinging output from the estimation model.

4. The waist swinging estimation device according to claim 1, wherein:

the estimation model is configured to output an estimated value regarding the waist swinging according to an input of the second feature amount corresponding to an average value or a difference regarding the first feature amount and the gait parameter for both feet, the at least one processor is configured to execute the instructions to:

calculate, as the second feature amount, the average value and the difference regarding the first feature amount and the gait parameter to be used for estimation of the waist swinging among the first feature amount and the gait parameter for both feet of the subject;

input the calculated second feature amount to the estimation model; and estimate waist swinging of the subject according to an estimated value regarding the waist swinging output from the estimation model, and wherein the average value is $(L+R)/2$ and the difference is an absolute difference $|L-R|$, each computed for corresponding gait phases of the left and right feet.

5. The waist swinging estimation device according to claim 4, wherein wherein:

the estimation model is configured to output an estimated value regarding the waist swinging according to an input of an attribute of the subject and the second feature amount, the at least one processor is configured to execute the instructions to:

input an attribute of the subject and the second feature amount to the estimation model; and estimate waist swinging of the subject according to an estimated value regarding the waist swinging output from the estimation model, and wherein the attribute of the subject comprises at least one of body weight, height, age, and gender, and is stored in the storage unit.

6. The waist swinging estimation device according to claim 1, wherein wherein:

the estimation model is configured to output a fluctuation width of the waist swinging regarding at least one of three directions of a traveling direction, a left-right direction, and a vertical direction in one gait cycle as an estimated value regarding the waist swinging according to an input of the feature amount data, the at least one processor is configured to execute the instructions to:

input the feature amount included in the acquired feature amount data to the estimation model; and estimate waist swinging of the subject according to the fluctuation width of the waist swinging regarding at least one of three directions of the traveling direction, the left-right direction, and the vertical direction output from the estimation model, and wherein the fluctuation width is defined as a difference between a maximum and a minimum of perpendicular distances from a linear-regression line of a waist-position time series over the one gait cycle detected by heel-contact and toe-off events.

7. An estimation system comprising:

the waist swinging estimation device according to claim 1; and the measurement device installed mounted on the footwear of the subject who is an estimation target of waist swinging that is an index regarding movement of the waist, wherein the measurement device includes:

the sensor configured to:

measure a spatial acceleration and a spatial angular velocity;

generate the sensor data regarding a movement of a foot by using the measured spatial acceleration and spatial angular velocity;

and output the generated sensor data;

the at least one memory storing the instructions; and wherein the at least one processor connected to the at least one memory is configured to execute the instructions to:

acquire time-series data of the sensor data measured by the sensor;

extract gait waveform data for one gait cycle from the time-series data of the sensor data;

normalize the extracted gait waveform data;

extract a feature amount used for estimation of the waist swinging from the normalized gait waveform data from a gait phase cluster configured by at least one temporally continuous gait phase;

generate feature amount data including the extracted feature amounts; and output the generated feature amount data to the waist swinging estimation device.

8. The estimation system according to claim 7, wherein:

the waist swinging estimation device is mounted on a terminal device having a screen visually recognizable by the subject, and the at least one processor of the waist swinging estimation device is configured to execute the instructions to display information regarding the waist swinging estimated according to the movement of the foot of the subject on a screen of the terminal device.

9. A waist swinging estimation method causing a computer to execute:

acquiring feature-amount data generated by a measurement device mounted on footwear of the subject in a position corresponding to an arch of the subject, the feature-amount data being produced from time-series sensor data of spatial accelerations and spatial angular velocities measured by a sensor installed on footwear of left and right feet by (i) detecting heel-contact and toe-off gait events, (ii) first normalizing one gait cycle to 0-100%, (iii) second normalizing a stance/swing ratio to 60/40, and (iv) extracting first feature amounts from a gait-phase cluster selected by correlation analysis;

calculating second feature amounts as bilateral statistics including an average value and an absolute difference of at least the first feature amounts and gait parameters for both feet, and input the second feature amounts together with one or more subject attributes to an estimation model;

estimating the waist swinging of the subject according to an output of the estimation model; and outputting information according to waist swinging of the subject including the fluctuation width and feedback information for gait correction;

wherein the estimation model is a trained machine-learning model learned using, for a plurality of subjects, an attribute of the subject, a cluster feature amount generated according to a gait of the subject, and a gait parameter, is trained to correlate foot-movement patterns with waist-movement characteristics, and is configured to output, for one gait cycle, a fluctuation width of waist swinging in at least one of a traveling direction, a left-right direction, and a vertical direction, the fluctuation width being defined as a difference between a maximum and a minimum of perpendicular distances from a regression line of a waist-position time series over one gait cycle detected by heel-contact and toe-off events.

10. The waist swinging estimation method according to claim 9, wherein the estimation model is configured to output an estimated value regarding the waist swinging according to an input of a gait parameter included in the feature amount data in addition to the second feature amounts, and wherein the waist swinging estimation method causing the computer to execute:

acquiring the feature amount data including a gait parameter extracted from a gait waveform of the spatial acceleration and the spatial angular velocity included in the sensor data;

inputting the gait parameter included in the acquired feature amount data to the estimation model in addition to the second feature amounts; and estimating waist swinging of the subject according to the estimated value regarding the waist swinging output from the estimation model.

11. The waist swinging estimation method according to claim 10, wherein the estimation model is configured to output an estimated value regarding the waist swinging according to an input of the first feature amount included in the feature amount data in addition to the second feature amounts, and wherein the waist swinging estimation method causing the computer to execute:

acquiring the feature amount data including a first feature amount for each gait phase cluster extracted from a gait waveform of a spatial acceleration and a spatial angular velocity included in the sensor data;

input the first feature amount included in the acquired feature amount data to the estimation model in addition to the second feature amounts; and estimate waist swinging of the subject according to the estimated value regarding the waist swinging output from the estimation model.

12. The waist swinging estimation method according to claim 9, wherein the estimation model is configured to output an estimated value regarding the waist swinging according to an input of the second feature amount corresponding to an average value or a difference regarding the first feature amount and the gait parameter for both feet, wherein the waist swinging estimation method causing the computer to execute:

calculating, as the second feature amount, the average value and the difference regarding the first feature amount and the gait parameter to be used for estimation of the waist swinging among the first feature amount and the gait parameter for both feet of the subject;

inputting the calculated second feature amount to the estimation model; and estimating waist swinging of the subject according to an estimated value regarding the waist swinging output from the estimation model, and wherein the average value is (L+R)/2 and the difference is an absolute difference |L−R|, each computed for corresponding gait phases of the left and right feet.

13. The waist swinging estimation method according to claim 12, wherein the estimation model is configured to output an estimated value regarding the waist swinging according to an input of an attribute of the subject and the second feature amount, wherein the waist swinging estimation method causing the computer to execute:

inputting an attribute of the subject and the second feature amount to the estimation model; and estimating waist swinging of the subject according to an estimated value regarding the waist swinging output from the estimation model, and wherein the attribute of the subject comprises at least one of body weight, height, age, and gender, and is stored in the storage unit.

14. The waist swinging estimation method according to claim 9, wherein the estimation model is configured to output a fluctuation width of the waist swinging regarding at least one of three directions of a traveling direction, a left-right direction, and a vertical direction in one gait cycle as an estimated value regarding the waist swinging according to an input of the feature amount data, wherein the waist swinging estimation method causing the computer to execute:

inputting the feature amount included in the acquired feature amount data to the estimation model; and estimating waist swinging of the subject according to the fluctuation width of the waist swinging regarding at least one of three directions of the traveling direction, the left-right direction, and the vertical direction output from the estimation model, and wherein the fluctuation width is defined as a difference between a maximum and a minimum of perpendicular distances from a linear-regression line of a waist-position time series over the one gait cycle detected by heel-contact and toe-off events.

15. A non-transitory recording medium with a program recorded therein executed by a computer to execute:

acquiring feature-amount data generated by a measurement device mounted on footwear of the subject in a position corresponding to an arch of the subject, the feature-amount data being produced from time-series sensor data of spatial accelerations and spatial angular velocities measured by a sensor installed on footwear of left and right feet by (i) detecting heel-contact and toe-off gait events, (ii) first normalizing one gait cycle to 0-100%, (iii) second normalizing a stance/swing ratio to 60/40, and (iv) extracting first feature amounts from a gait-phase cluster selected by correlation analysis;

calculating second feature amounts as bilateral statistics including an average value and an absolute difference of at least the first feature amounts and gait parameters for both feet, and input the second feature amounts together with one or more subject attributes to an estimation model;

estimating the waist swinging of the subject according to an output of the estimation model; and outputting information according to waist swinging of the subject including the fluctuation width and feedback information for gait correction;

wherein the estimation model is a trained machine-learning model learned using, for a plurality of subjects, an attribute of the subject, a cluster feature amount generated according to a gait of the subject, and a gait parameter, is trained to correlate foot-movement patterns with waist-movement characteristics, and is configured to output, for one gait cycle, a fluctuation width of waist swinging in at least one of a traveling direction, a left-right direction, and a vertical direction, the fluctuation width being defined as a difference between a maximum and a minimum of perpendicular distances from a regression line of a waist-position time series over one gait cycle detected by heel-contact and toe-off events.

16. The non-transitory recording medium according to claim 15, wherein the estimation model is configured to output an estimated value regarding the waist swinging according to an input of a gait parameter included in the feature amount data in addition to the second feature amounts, and wherein the non-transitory recording medium with the program recorded therein executed by the computer to execute:

acquiring the feature amount data including a gait parameter extracted from a gait waveform of the spatial acceleration and the spatial angular velocity included in the sensor data;

inputting the gait parameter included in the acquired feature amount data to the estimation model in addition to the second feature amounts; and estimating waist swinging of the subject according to the estimated value regarding the waist swinging output from the estimation model.

17. The non-transitory recording medium according to claim 16, wherein the estimation model is configured to output an estimated value regarding the waist swinging according to an input of the first feature amount included in the feature amount data in addition to the second feature amounts, and wherein the non-transitory recording medium with the program recorded therein executed by the computer to execute:

acquiring the feature amount data including a first feature amount for each gait phase cluster extracted from a gait waveform of a spatial acceleration and a spatial angular velocity included in the sensor data;

inputting the first feature amount included in the acquired feature amount data to the estimation model in addition to the second feature amounts; and estimating waist swinging of the subject according to the estimated value regarding the waist swinging output from the estimation model.

18. The non-transitory recording medium according to claim 15, wherein the estimation model is configured to output an estimated value regarding the waist swinging according to an input of the second feature amount corresponding to an average value or a difference regarding the first feature amount and the gait parameter for both feet, wherein the non-transitory recording medium with the program recorded therein executed by the computer to execute:

calculating, as the second feature amount, the average value and the difference regarding the first feature amount and the gait parameter to be used for estimation of the waist swinging among the first feature amount and the gait parameter for both feet of the subject;

inputting the calculated second feature amount to the estimation model; and estimating waist swinging of the subject according to an estimated value regarding the waist swinging output from the estimation model, and wherein the average value is (L+R)/2 and the difference is an absolute difference |L−R|, each computed for corresponding gait phases of the left and right feet.

19. The non-transitory recording medium according to claim 18, wherein the estimation model is configured to output an estimated value regarding the waist swinging according to an input of an attribute of the subject and the second feature amount, wherein the non-transitory recording medium with the program recorded therein executed by the computer to execute:

inputting an attribute of the subject and the second feature amount to the estimation model; and estimating waist swinging of the subject according to an estimated value regarding the waist swinging output from the estimation model, and wherein the attribute of the subject comprises at least one of body weight, height, age, and gender, and is stored in the storage unit.

20. The non-transitory recording medium according to claim 15, wherein the estimation model is configured to output a fluctuation width of the waist swinging regarding at least one of three directions of a traveling direction, a left-right direction, and a vertical direction in one gait cycle as an estimated value regarding the waist swinging according to an input of the feature amount data, wherein the non-transitory recording medium with the program recorded therein executed by the computer to execute:

inputting the feature amount included in the acquired feature amount data to the estimation model; and estimating waist swinging of the subject according to the fluctuation width of the waist swinging regarding at least one of three directions of the traveling direction, the left-right direction, and the vertical direction output from the estimation model, and wherein the fluctuation width is defined as a difference between a maximum and a minimum of perpendicular distances from a linear-regression line of a waist-position time series over the one gait cycle detected by heel-contact and toe-off events.

* * * * *